US011857731B2

(12) United States Patent
Guo et al.

(10) Patent No.: US 11,857,731 B2
(45) Date of Patent: Jan. 2, 2024

(54) LIGHT ADJUSTMENT METHOD AND TERMINAL

(71) Applicant: HUAWEI TECHNOLOGIES CO., LTD., Shenzhen (CN)

(72) Inventors: Guangming Guo, Shenzhen (CN); Xiaoping Huang, Shanghai (CN); Xi Huang, Shenzhen (CN); Chenxi Lu, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 507 days.

(21) Appl. No.: 17/059,224

(22) PCT Filed: May 28, 2019

(86) PCT No.: PCT/CN2019/088732
§ 371 (c)(1),
(2) Date: Nov. 26, 2020

(87) PCT Pub. No.: WO2019/228323
PCT Pub. Date: Dec. 5, 2019

(65) Prior Publication Data
US 2021/0205573 A1 Jul. 8, 2021

(30) Foreign Application Priority Data
May 29, 2018 (CN) .......................... 201810537359.0

(51) Int. Cl.
*A61M 21/02* (2006.01)
*A61B 5/00* (2006.01)
(Continued)

(52) U.S. Cl.
CPC .......... *A61M 21/02* (2013.01); *A61B 5/4815* (2013.01); *A61M 2021/0044* (2013.01); *G06F 3/0482* (2013.01); *G06F 3/04847* (2013.01)

(58) Field of Classification Search
CPC .......... A61M 21/02; A61M 2021/0044; A61B 5/4815; G06F 3/0482; G06F 3/04847;
(Continued)

(56) References Cited

U.S. PATENT DOCUMENTS 5,589,741 A 12/1996 Terman et al.
7,520,607 B2 4/2009 Casper et al.
(Continued)

FOREIGN PATENT DOCUMENTS

CN 101547248 A 9/2009
CN 104010082 A 8/2014
(Continued)

OTHER PUBLICATIONS

Sadeghniiat-Haghighi, Khosro et al. Efficacy and Hypnotic Effects of Melatonin in Shift-Work Nurses: Double-Blind, Placebo-Controlled Crossover Trial. Journal of Circadian Rhythms 6 (2008): 10. PMC. Web. Aug. 30, 2017, 5 pages.
(Continued)

*Primary Examiner* — Sunita Reddy

(57) ABSTRACT

Various embodiments relate to the field of communications technologies, and provide a light adjustment method and a terminal to resolve a problem that an existing light therapy device cannot flexibly adjust light based on a light requirement of a user and cannot more intelligently adjust a circadian rhythm of the user. In those embodiments, an awake time period and a sleep time period of a user is determined by the terminal, and parameter thresholds in the awake time period and the sleep time period is determined by the terminal. In those embodiments, a light parameter in a current time period is obtain by the terminal, and based on the light parameter in the current time period, a light parameter of light emitted by a light source device is then adjusted by the terminal.

17 Claims, 15 Drawing Sheets

(51) Int. Cl.
*A61M 21/00* (2006.01)
*G06F 3/0482* (2013.01)
*G06F 3/04847* (2022.01)

(58) Field of Classification Search
CPC .......... A61N 2005/0626; A61N 5/0618; A61N 5/0613; A61N 2005/0627
USPC ...................................................... 600/26–28
See application file for complete search history.

(56) References Cited

U.S. PATENT DOCUMENTS

| | | | |
|---|---|---|---|
| 7,748,845 B2 | 7/2010 | Casper et al. | |
| 2006/0106437 A1* | 5/2006 | Czeisler | A61M 21/02 607/88 |
| 2007/0282159 A1* | 12/2007 | Sato | A61M 21/00 600/27 |
| 2009/0207028 A1 | 8/2009 | Kubey et al. | |
| 2010/0130833 A1* | 5/2010 | Mott | A61N 5/0618 600/26 |
| 2011/0010014 A1* | 1/2011 | Oexman | F24F 11/63 600/301 |
| 2012/0233563 A1* | 9/2012 | Chakra | G06Q 10/1093 715/772 |
| 2012/0296400 A1* | 11/2012 | Bierman | A61N 5/0618 607/88 |
| 2012/0303099 A1* | 11/2012 | D'Ambrosio | A61N 5/0618 607/90 |
| 2014/0052220 A1* | 2/2014 | Pedersen | A61M 21/00 607/88 |
| 2015/0148871 A1* | 5/2015 | Maxik | G16H 20/70 607/88 |
| 2015/0174361 A1* | 6/2015 | Baaijens | A61M 21/02 600/27 |
| 2015/0366024 A1 | 12/2015 | Chen | |
| 2017/0065792 A1 | 3/2017 | Bonvallet et al. | |
| 2017/0135182 A1 | 5/2017 | Chen | |
| 2017/0182283 A1* | 6/2017 | Palmateer | A61B 5/4812 |
| 2017/0189641 A1* | 7/2017 | Moturu | G16H 40/67 |
| 2018/0144714 A1 | 5/2018 | Khorasani et al. | |
| 2018/0339127 A1* | 11/2018 | Van Reen | A61M 21/02 |
| 2019/0209806 A1* | 7/2019 | Allen | G16H 40/67 |
| 2019/0350066 A1* | 11/2019 | Herf | H05B 47/105 |
| 2021/0176841 A1* | 6/2021 | Borra | H05B 47/17 |

FOREIGN PATENT DOCUMENTS

| | | |
|---|---|---|
| CN | 104540264 A | 4/2015 |
| CN | 104796537 A | 7/2015 |
| CN | 104932855 A | 9/2015 |
| CN | 105339043 A | 2/2016 |
| CN | 105612816 A | 5/2016 |
| CN | 105873319 A | 8/2016 |
| CN | 103338817 B | 11/2016 |
| CN | 106453896 A | 2/2017 |
| CN | 106921784 A | 7/2017 |
| CN | 107197576 A | 9/2017 |
| CN | 107708191 A | 2/2018 |
| CN | 107870575 A | 4/2018 |
| CN | 107926091 A | 4/2018 |
| JP | 4424278 B2 | 3/2010 |
| KR | 20170096621 A | 8/2017 |
| WO | 2012146256 A2 | 11/2012 |

OTHER PUBLICATIONS

Waldhauser F, Saletu B, Trinchard-Lugan I. Sleep laboratory investigations on hypnotic properties of melatonin[J]. Psychopharmacology, 1990, 100(2): 222-226.
Lewy, Alfred J., et al. "Light suppresses melatonin secretion in humans." Science 210.4475 (1980): 1267-1269.
Berson, David M., Felice A. Dunn, and Motoharu Takao. "Phototransduction by retinal ganglion cells that set the circadian clock." Science 295.5557 (2002): 1070-1073.
Thapan, Kavita, Josephine Arendt, and Debra J. Skene. "An action spectrum for melatonin suppression: evidence for a novel non rod, non cone photoreceptor system in humans." The Journal of physiology 535.1 (2001): 261-267.
Gooley, Joshua J., et al. "Spectral responses of the human circadian system depend on the irradiance and duration of exposure to light." Science translational medicine 2.31 (2010): 31ra33-31ra33, 21 pages.
Notice of Allowance for Chinese Application No. 201810537359.0 dated Apr. 6, 2021, 5 pages.
Office Action for Chinese Application No. 201810537359.0 dated Apr. 9, 2020, 10 pages.
Office Action for Chinese Application No. 201810537359.0 dated Dec. 28, 2020, 8 pages.
European Search Report for Application No. 19812146.9, dated Jun. 9, 2021, 7 pages.
PCT Search Report for Application No. PCT/CN2019/088732, dated Aug. 21, 2019, 9 pages.

\* cited by examiner

LIGHT ADJUSTMENT METHOD AND TERMINAL

CROSS-REFERENCE TO RELATED APPLICATIONS

This application is a National Stage of International Application No. PCT/CN2019/088732, filed on May 28, 2019, which claims priority to Chinese Patent Application No. 201810537359.0, filed on May 29, 2018. Both of the aforementioned applications are hereby incorporated by reference in their entireties.

TECHNICAL FIELD

Embodiments of this application relate to the field of communications technologies, and in particular, to a light adjustment method and a terminal.

BACKGROUND

According to related statistics, due to work pressure, issues associated with light pollution, and the like, there is a gradually increasing proportion of users suffering from lack of sleep or insomnia. One of the reasons for lack of sleep or insomnia is endogenous melatonin secretion disorder. As a hormone secreted by the pineal gland of the brain, melatonin plays an important role in regulating a circadian rhythm, sleep, immunity, and the like of a human body. Usually, more melatonin is secreted at night than in the daytime. At night, melatonin can shorten a time from being awake to falling asleep, making a user sleep fast and reducing a quantity of times of waking up at night, thereby improving sleep quality of the user.

In addition, there is an experiment indicating that a secretion amount of melatonin is related to light received by a user. Usually, the user receives relatively sufficient light in the daytime, and the total light includes specific light that can result in suppressing secretion of melatonin, and therefore the secretion amount of melatonin is relatively small. At night, the user receives relatively weak light, and therefore the secretion amount of melatonin increases.

Based on impact of light on the secretion amount of melatonin, the prior art provides a light therapy device to regulate sleep quality of a user by providing light with different levels of intensity for stimulating melatonin to play different roles in regulating a secretion level of melatonin. However, there is a difference between different users, different users may have different light requirements, and one user has different light requirements in different scenarios. The existing light therapy device cannot flexibly adjust light based on a light requirement of the user, and consequently a circadian rhythm of the user cannot be more intelligently adjusted.

SUMMARY

Embodiments of this application provide a light adjustment method and a terminal to adjust, based on a user requirement, light received by a user, so as to more intelligently adjust a circadian rhythm of the user.

To achieve the foregoing objective, the following technical solutions are used in the embodiments of this application:

According to a first aspect, an embodiment of this application provides a light adjustment method, including a terminal determines an awake time period and a sleep time period of a user; determines light parameter thresholds in the awake time period and the sleep time period; obtains a light parameter in a current time period; and adjusts, based on the light parameter in the current time period, a light parameter of light emitted by a light source device. The current time period is the awake time period or the sleep time period.

In a possible design, the awake time period and the sleep time period each include at least one first sub-period and/or second sub-period, the first sub-period is a daytime period, and the second sub-period is a nighttime period.

The time period is divided based on a finer time granularity, so that improved real-time performance is achieved in detecting the light parameter of the user by the terminal.

In a possible design, the determining an awake time period and a sleep time period of a user may be specifically implemented by the terminal receiving time period division data entered by the user, and determining the awake time period and the sleep time period of the user based on the time period division data. Alternatively, the terminal obtains a first user profile of the user, and determines the awake time period and the sleep time period of the user based on the first user profile.

The first user profile includes a user behavior and a sleep status, and the sleep status is used to describe sleep quality of the user.

In a possible design, that the terminal determines light parameter thresholds in the awake time period and the sleep time period may be specifically implemented as follows. The terminal obtains a second user profile and/or geographical location information of the user, and determines a light parameter threshold in each first sub-period and a light parameter threshold in each second sub-period based on the second user profile and/or the geographical location information of the user.

In a possible design, that the terminal determines light parameter thresholds in the awake time period and the sleep time period may be alternatively implemented as follows. If a user profile similarity between a target user and the user is greater than a threshold, the terminal respectively determines a light parameter threshold of the target user in each daytime period and a light parameter threshold of the target user in each nighttime period as a light parameter threshold in each first sub-period and a light parameter threshold in each second sub-period. The user profile similarity is used to describe a similarity between second user profiles.

In a possible design, the light parameter threshold includes a lower light parameter threshold and an upper light parameter threshold.

That the terminal adjusts, based on the light parameter in the current time period, a light parameter of light emitted by a light source device may be specifically implemented as follows: If it is determined that a light parameter in the current sub-period is less than a lower light parameter threshold in the current sub-period, the terminal adjusts a light parameter of light emitted by the light source device in a next sub-period of the current sub-period to a first light parameter. The current sub-period is the first sub-period or the second sub-period, and the first light parameter is greater than the light parameter in the current sub-period.

Alternatively, if it is determined that a light parameter in the current sub-period is greater than an upper light parameter threshold in the current sub-period, the terminal adjusts a light parameter of light emitted by the light source device in a next sub-period of the current sub-period to a second light parameter. The second light parameter is less than the light parameter in the current sub-period.

In a possible design, after determining the light parameter thresholds in the awake time period and the sleep time period, the terminal may further perform the following operations: The terminal determines a total amount of light received in all daytime periods, and if it is determined that the total amount of light received in all the daytime periods is greater than an upper threshold of the total amount of light in the daytime periods, the terminal adjusts a light parameter of the light source device in a nighttime period to a third light parameter. A third light parameter in a single nighttime period is less than a preset light parameter in the single nighttime period.

Alternatively, if it is determined that the total amount of light received in all the daytime periods is less than a lower threshold of the total amount of light in the daytime periods, the terminal adjusts a light parameter of the light source device in a nighttime period to a fourth light parameter. A fourth light parameter in a single nighttime period is greater than a preset light parameter in the single nighttime period.

According to the method for adjusting a light parameter in a nighttime period, a light parameter threshold in each nighttime period may be determined again based on a light parameter received by the user in the daytime. In this way, a light parameter received by the user in the nighttime period better meets a user requirement, thereby further improving a circadian rhythm of the user.

In a possible design, after determining the light parameter thresholds in the awake time period and the sleep time period, the terminal may further perform the following operation: If the current sub-period is a sleep latency, the terminal adjusts a percentage of a target type of light in light emitted by the light source device to 0. The target type of light is light related to regulation of a circadian rhythm, and the sleep latency is a first sub-period or a second sub-period that is included in the awake time period and that is before and adjacent to the sleep time period.

According to the light adjustment method, light stimulation received by the user in the sleep latency can be reduced, and the user can fall asleep more quickly.

In a possible design, that the terminal adjusts a light parameter of light emitted by a light source device may be specifically implemented as follows. The terminal sends a light adjustment instruction to a target terminal, to instruct the target terminal to adjust the light parameter of the light emitted by the light source device.

According to the method, the target terminal that provides a better light parameter adjustment effect may provide light adjustment for the user, to enhance a light adjustment effect.

According to a second aspect, an embodiment of this application provides a terminal. A memory and a processor are disposed in the terminal.

The memory is configured to store information including a program instruction. The processor is configured to: determine an awake time period and a sleep time period of a user; determine light parameter thresholds in the awake time period and the sleep time period; obtain a light parameter in a current time period, where the current time period is the awake time period or the sleep time period; and adjust, based on the light parameter in the current time period, a light parameter of light emitted by a light source device.

In a possible design, the awake time period and the sleep time period each include at least one first sub-period and/or second sub-period, the first sub-period is a daytime period, and the second sub-period is a nighttime period.

In a possible design, that the processor is configured to determine an awake time period and a sleep time period of a user specifically includes the processor being configured to receive time period division data entered by the user, and determine the awake time period and the sleep time period of the user based on the time period division data. Alternatively, the processor is configured to obtain a first user profile of the user, and determine the awake time period and the sleep time period of the user based on the first user profile. The first user profile includes a user behavior and a sleep status, and the sleep status is used to describe sleep quality of the user.

In a possible design, that the processor is configured to determine light parameter thresholds in the awake time period and the sleep time period specifically includes the processor being configured to obtain a second user profile and/or geographical location information of the user, and determine a light parameter threshold in each first sub-period and a light parameter threshold in each second sub-period based on the second user profile and/or the geographical location information of the user.

In a possible design, that the processor is configured to determine light parameter thresholds in the awake time period and the sleep time period specifically includes the processor being configured to respectively determine a light parameter threshold of the target user in each daytime period and a light parameter threshold of the target user in each nighttime period as a light parameter threshold in each first sub-period and a light parameter threshold in each second sub-period if a user profile similarity between a target user and the user is greater than a threshold. The user profile similarity is used to describe a similarity between second user profiles.

In a possible design, the light parameter threshold includes a lower light parameter threshold and an upper light parameter threshold.

That the processor is configured to adjust, based on the light parameter in the current time period, a light parameter of light emitted by a light source device specifically includes the processor being configured to adjust a light parameter of light emitted by the light source device in a next sub-period of the current sub-period to a first light parameter if it is determined that a light parameter in the current sub-period is less than a lower light parameter threshold in the current sub-period, or adjust a light parameter of light emitted by the light source device in a next sub-period of the current sub-period to a second light parameter if it is determined that a light parameter in the current sub-period is greater than an upper light parameter threshold in the current sub-period. The current sub-period is the first sub-period or the second sub-period, the first light parameter is greater than the light parameter in the current sub-period, and the second light parameter is less than the light parameter in the current sub-period.

In a possible design, after determining the light parameter thresholds in the awake time period and the sleep time period, the processor is further configured to: determine a total amount of light received in all daytime periods, and adjust a light parameter of the light source device in a nighttime period to a third light parameter if it is determined that the total amount of light received in all the daytime periods is greater than an upper threshold of the total amount of light in the daytime periods, or adjust a light parameter of the light source device in a nighttime period to a fourth light parameter if it is determined that the total amount of light received in all the daytime periods is less than a lower threshold of the total amount of light in the daytime periods. A third light parameter in a single nighttime period is less than a preset light parameter in the single nighttime period, and a fourth light parameter in a single nighttime period is greater than a preset light parameter in the single nighttime period.

In a possible design, after determining the light parameter thresholds in the awake time period and the sleep time period, the processor is further configured to adjust a percentage of a target type of light in light emitted by the light source device to 0 if the current sub-period is a sleep latency. The target type of light is light related to regulation of a circadian rhythm, and the sleep latency is a first sub-period or a second sub-period that is included in the awake time period and that is before and adjacent to the sleep time period.

In a possible design, the transceiver is configured to send a light adjustment instruction to a target terminal, to instruct the target terminal to adjust the light parameter of the light emitted by the light source device.

According to a third aspect, an embodiment of this application provides a terminal. The terminal has a function of implementing the method according to any one of the first aspect or the possible designs of the first aspect. The function may be implemented by hardware, or may be implemented by hardware by executing corresponding software. The hardware or software includes one or more modules corresponding to the function.

According to a fourth aspect, a terminal is provided, and includes a processor and a memory. The memory is configured to store a computer-executable instruction, and when the terminal runs, the processor executes the computer-executable instruction stored in the memory, so that the terminal performs the light adjustment method according to any one of the first aspect or the possible designs of the first aspect.

According to a fifth aspect, a terminal is provided, and includes a processor. The processor is configured to: be coupled to a memory; read an instruction in the memory; and perform the light adjustment method according to any one of the first aspect or the possible designs of the first aspect based on the instruction.

According to a sixth aspect, a computer-readable storage medium is provided. The computer-readable storage medium stores an instruction, and when the instruction runs on a computer, the computer is enabled to perform the light adjustment method according to any one of the first aspect or the possible designs of the first aspect.

According to a seventh aspect, a computer program product that includes an instruction is provided. When the computer program product runs on a computer, the computer is enabled to perform the light adjustment method according to any one of the first aspect or the possible designs of the first aspect.

According to an eighth aspect, a circuit system is provided. The circuit system includes a processing circuit, and the processing circuit is configured to support a terminal in implementing the function in the first aspect.

For technical effects brought by any design manner of the second to the eighth aspects, refer to the technical effects brought by different design manners of the first aspect. Details are not described herein again.

DESCRIPTION OF EMBODIMENTS

The following terms "first" and "second" are merely intended for a purpose of description, and shall not be understood as an indication or implication of relative importance, order, or implicit indication of the number of indicated technical features. Therefore, a feature limited by "first" or "second" may explicitly or implicitly include one or more features. In the description of the embodiment of this application, unless otherwise stated, "multiple" means two or more than two.

Terms in various embodiments are first described.

Intrinsically photosensitive retinal ganglion cells are main cells on which melatonin synthesis and release depend. Usually, the ipRGC senses an optical signal, and passes the optical signal through the optic nerve to the suprachiasmatic nucleus (SCN) of the hypothalamus and other nervous nuclei. The SCN and the other nervous nuclei regulate a circadian rhythm, including regulating secretion and release of a specific hormone. The specific hormone includes melatonin.

Figure 1:
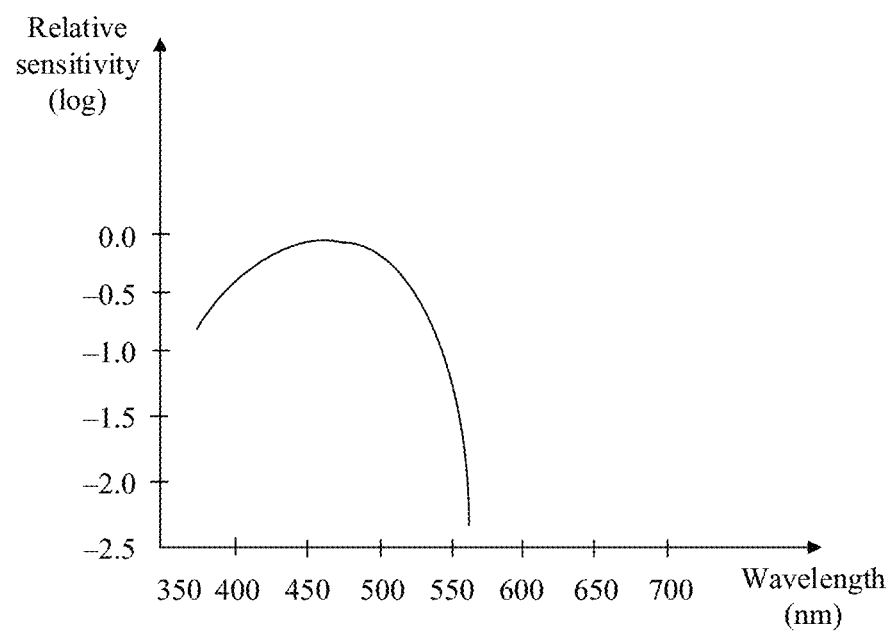
FIG. 1 is an example schematic diagram of ipRGC sensitive band light.

Usually, ipRGC sensitive band light is visible light whose wavelength falls within a band range of 380 nm to 550 nm and whose peak value is 480 nm. FIG. 1 shows a response curve of ipRGC to light in different bands. In FIG. 1, the ipRGC is more sensitive to visible light whose wavelength falls within a band range of 380 nm to 550 nm. It may be understood that in the daytime, a percentage of light in the band in light received by an eye is usually relatively high. This may stimulate the ipRGC, so that the SCN decreases a secretion amount of melatonin, to alleviate sleepiness. At night, a percentage of light in the band in light received by the eye is relatively low. This may stimulate the ipRGC, so that the SCN increases the secretion amount of melatonin, to improve sleep quality of a user. Herein, that the wavelength ranges from 380 nm to 550 nm is merely an example. A person skilled in the art may obtain light that is in another band and that is used to regulate a circadian rhythm. This is not limited in this application.

In the prior art, a light therapy device is provided to adjust emitted light and provide a sleep assistance function for a user. The light therapy device may provide light with different brightness levels for the user. For example, the light therapy device provides daytime light 1 with a brightness level of 1, and the daytime light 1 may be used to wake up the user in the morning to improve working efficiency. At night, the light therapy device provides nighttime light 2 with a brightness level of 2, and the nighttime light 2 may be used for sleep assistance at night because of low brightness. Further, brightness of the nighttime light 2 may be set to a gradually fading mode, making it easier for the user to sleep.

However, in many application scenarios, light required by the user is not necessarily consistent with light provided by the light therapy device. For example, in a time period from 13:00 to 14:00, a body temperature of the user decreases after lunch, and the user is in a fatigue state. In this case, if the light therapy device provides the daytime light 1 for the user, excitability of the brain of the user is improved, which is unfavorable to lunch break of the user.

It may be learned that a limited quantity of brightness levels are set for the existing light therapy device, and various types of brightness provided by the light therapy device are relatively fixed. Consequently, light provided by the light therapy device may not meet a real-time requirement of a user, and a method for improving sleep quality is not intelligent enough.

In view of this, an embodiment in accordance with the present disclosure provides a light adjustment method. The method may be applied to a system shown in FIG. 2. The system includes a terminal 20 and a server 21 that can communicate with the terminal. In some embodiments, the system further includes a light source device 22.

Figure 2:
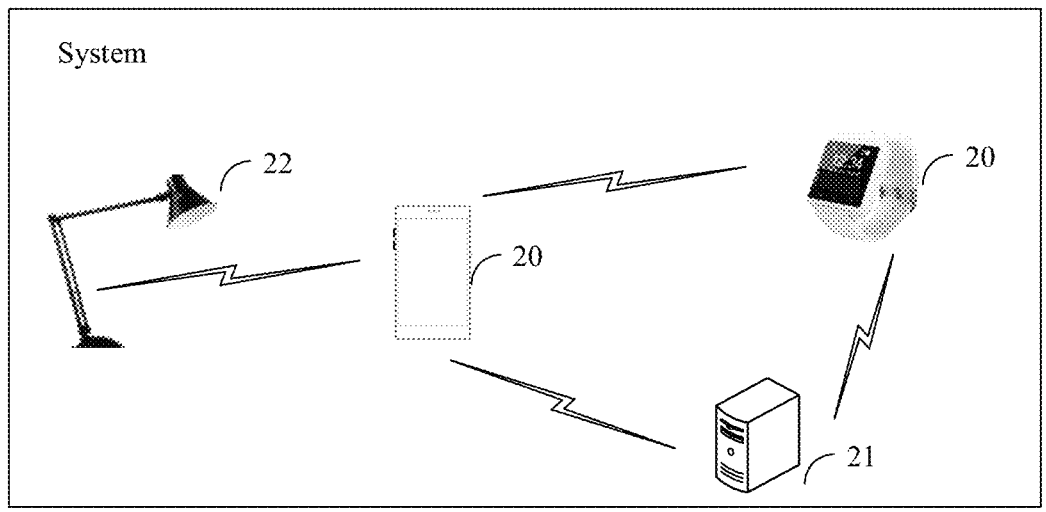
FIG. 2 is a schematic diagram of a system architecture according to an embodiment of this application.

The terminal 20 may be a mobile phone or a wearable device (such as a wristband, a watch, or a pair of glasses) shown in FIG. 2, or may be any terminal with a light detection function, for example, a tablet computer, a notebook computer, an ultra-mobile personal computer (ultra-mobile personal computer, UMPC), or a netbook that is not shown in FIG. 2. This is not limited in this embodiment of this application.

Referring to FIG. 2, the terminal may obtain a second user profile of a user and geographical location information of the user. Herein, the user profile includes but is not limited to a user behavior, a user type, and a user sleep status. In an example of obtaining the sleep status, the wearable device (for example, the wristband in FIG. 2) collects sleep data of the user, and feeds back the sleep data to the mobile phone. Alternatively, in a smart household scenario, a smart household object (for example, a smart mattress that is not shown in FIG. 2) collects sleep data of the user, to reflect the sleep status of the user. Certainly, the mobile phone or the wristband may alternatively obtain the sleep data of the user from the server 21.

Then, the terminal determines a light parameter threshold in each sub-period based on the second user profile and the geographical location information of the user.

Subsequently, the terminal may detect a light parameter of light received by the user in a current sub-period, and adjust, based on the light parameter in the current sub-period and a light parameter threshold in the sub-period, a light parameter of light emitted by the light source device.

The light source device may be disposed inside the terminal, for example, disposed inside the mobile phone. In this case, the mobile phone adjusts the light parameter of the light emitted by the internal light source device (for example, a light source device in a screen of the mobile phone). The light source device may alternatively be disposed independently. For example, the light source device may be a lamp 22 shown in FIG. 2. In this case, after determining that the light parameter in the current sub-period cannot meet a user requirement, the mobile phone may adjust a light parameter of light emitted by the lamp. Certainly, the independent light source device in this embodiment of this application is not limited to a form of a lamp, and may alternatively be another device that includes a light source and that is used for lighting. This is not limited in this embodiment of this application.

Figure 3:
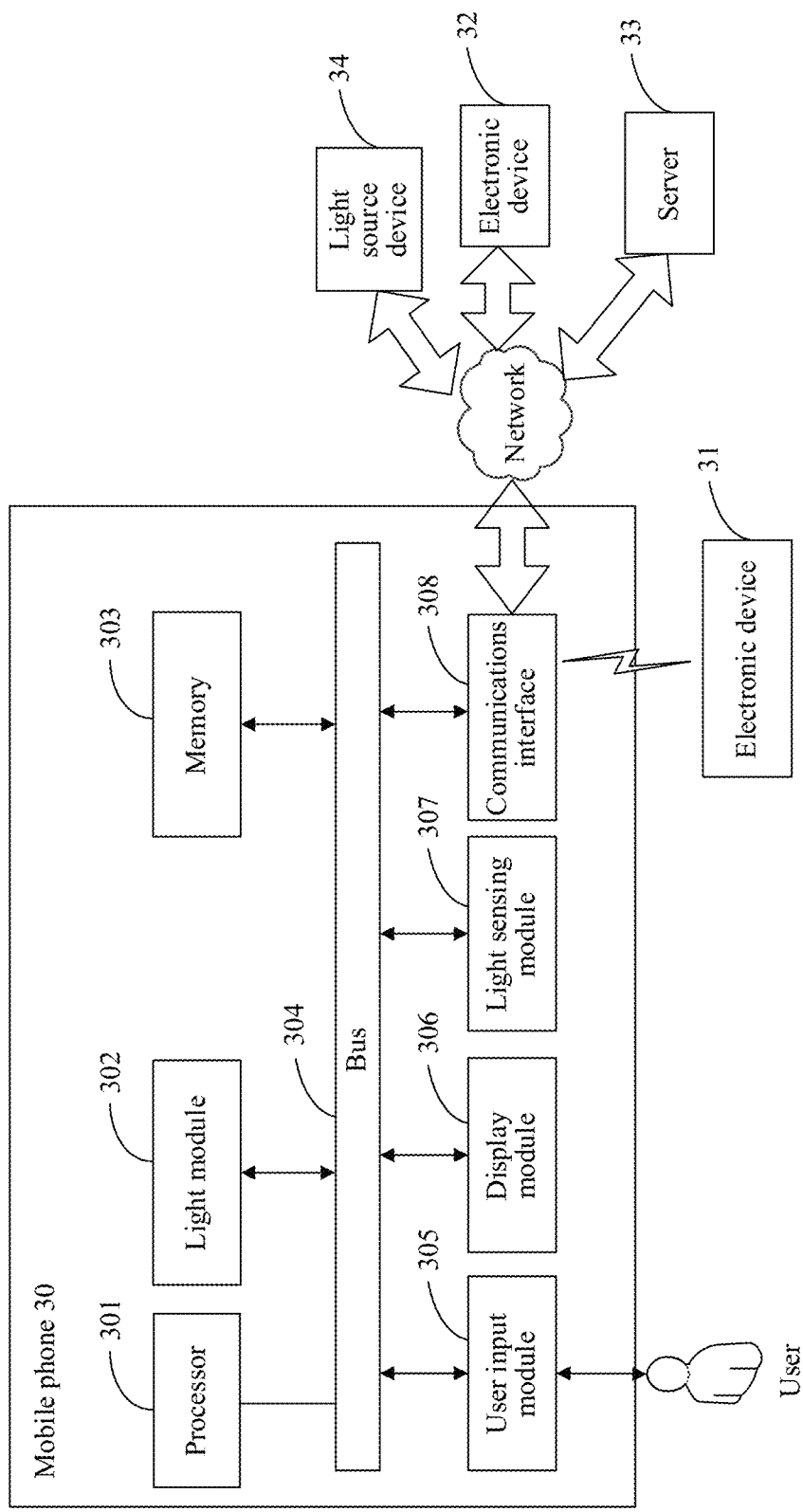
FIG. 3 is a schematic structural diagram of a mobile phone according to an embodiment of this application.

As shown in FIG. 3, a mobile phone 30 is used as an example to describe this embodiment in detail. It should be understood that the mobile phone 30 shown in the figure is merely an example of the terminal, and the mobile phone 30 may include more or fewer components than those shown in FIG. 2, may combine two or more components, or may have different component configurations.

Referring to FIG. 3, the mobile phone 30 may communicate with electronic devices 31 and 32 and a server 33 other than the mobile phone 30. It may be understood that the electronic device 31 or 32 may be the light source device shown in FIG. 2. The mobile phone 30 may include a processor 301, a memory 303, a bus 304, a user input module 305, a display module 306, a light sensing module 307, a communications interface 308, and other similar and/or suitable components.

The bus 304 may be a circuit that interconnects the foregoing elements and transfers communication (for example, a control message) between the elements.

The light sensing module 307 may detect a light parameter received by the mobile phone, and transfer the detected light parameter to the processor 301. The light sensing module 307 mainly detects the foregoing ipRGC sensitive band light. For detailed description of the ipRGC sensitive band light, refer to the foregoing description. Details are not described herein again.

The processor 301 may receive a command from the foregoing another element (for example, the memory 303, the user input module 305, the display module 306, or the communications interface 308) by using the bus 304, may interpret the received command, and may perform calculation or data processing based on the interpreted command. For example, the processor 301 receives light intensity detected by the light sensing module 307, calculates, based on the light intensity, an amount of light received by a user in a current sub-period, and then determines whether a light parameter of light emitted by a light source device needs to be adjusted. Herein, the light source device may be an independent device, or may be a light source device disposed inside the mobile phone. In some embodiments, as shown in FIG. 3, when the light source device is disposed inside the mobile phone, the mobile phone may further include a light module 302.

The memory 303 may store a command or data received from the processor 301 or another element (for example, the user input module 305, the display module 306, or the communications interface 308), or a command or data generated by the processor 301 or another element.

The user input module 305 may receive a command or data entered by the user by using an input-output means (for example, a sensor, a keyboard, or a touchscreen), and may transfer the received command or data to the processor 301 or the memory 303 by using the bus 304.

The display module 306 may display various types of information (for example, multimedia data and text data) received from the foregoing element. For example, the display module 306 may display a video, an image, or data to the user.

The communications interface 308 may control a short-range communications connection between the mobile phone 30 and the electronic device 31. When the mobile phone 30 is paired with the electronic device, the communications interface 308 may stop a scanning operation of waiting for receiving a signal from an adjacent electronic device, or stop a broadcast operation of broadcasting a signal. For example, in response to pairing between the mobile phone 30 and the electronic device 31, the communications interface 308 stops the scanning operation of waiting for receiving a signal from an adjacent electronic device, or stops the broadcast operation of broadcasting a signal. When the mobile phone 30 is paired with the electronic device, the communications interface 308 may control a period of the scanning or broadcast operation.

In addition, according to the embodiments disclosed in this application, the mobile phone 30 may further communicate with another device by using the communications interface 308. For example, the mobile phone 30 may communicate with the another electronic device 32 and the server 33 by using the communications interface 308. Certainly, when the light source device is an independent device, to adjust the light parameter of the light source device, the mobile phone 30 may further communicate with a light source device 34 shown in FIG. 3. Specifically, the communications interface 308 may communicate with the another electronic device 32, the server 33, the light source device 34, or the like directly or by using a network. For example, the communications interface 308 may perform an operation of connecting the mobile phone 30 to a network.

Figure 4A:
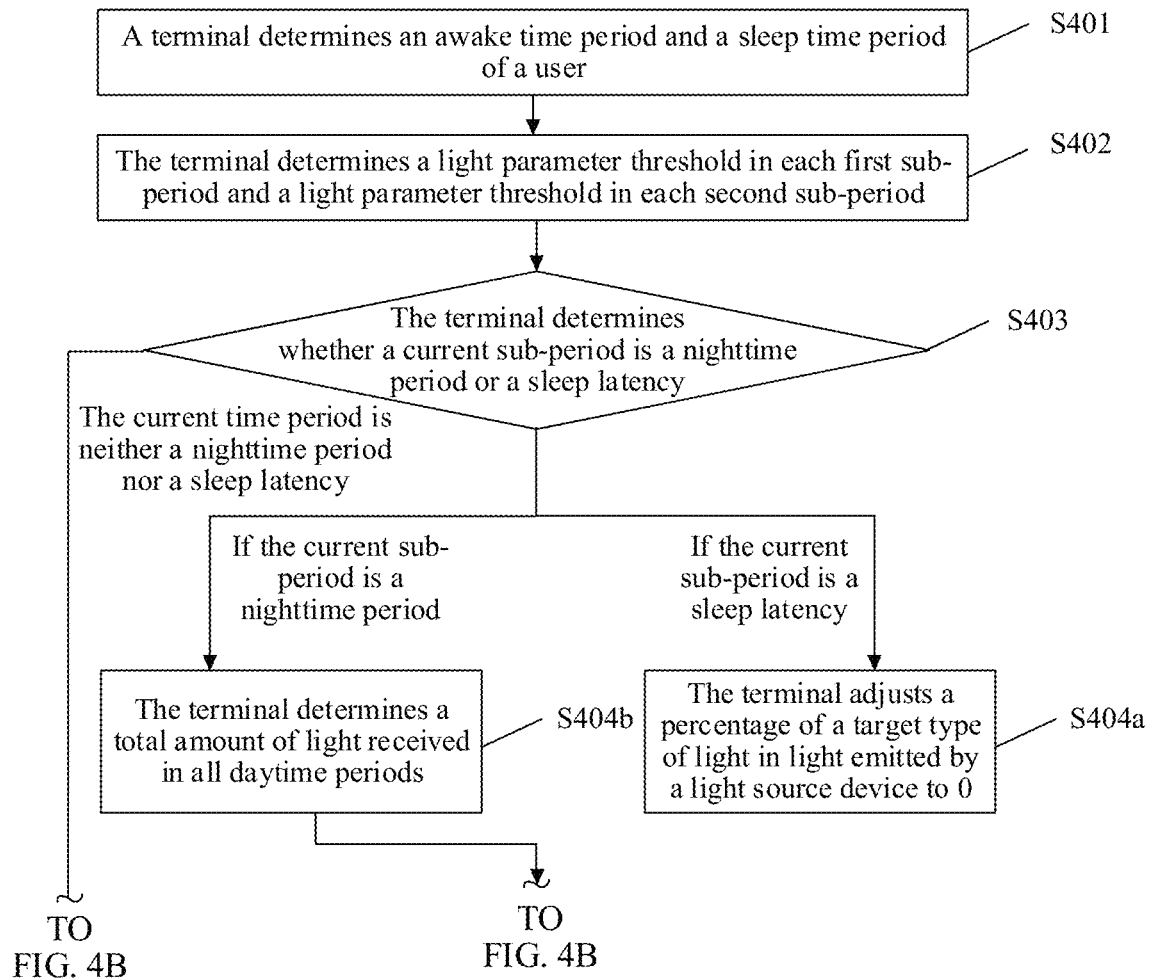
FIG. 4A and FIG. 4B are schematic flowchart of a light adjustment method according to an embodiment of this application.
Figure 4B:
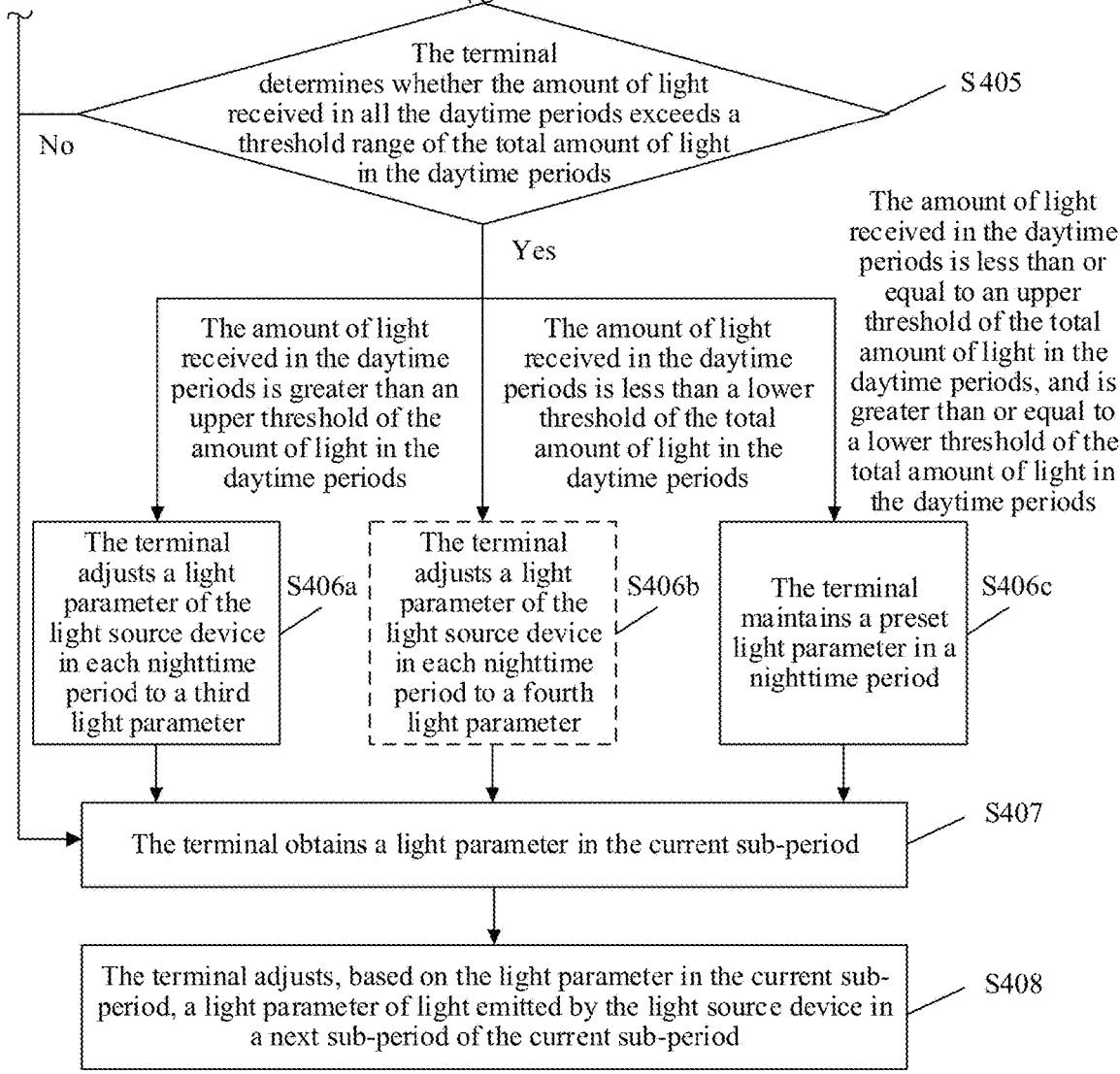

An embodiment in accordance with the present disclosure provides a light adjustment method. As shown in FIG. 4A and FIG. 4B, the method includes S401 to S408.

S401. A terminal determines an awake time period and a sleep time period of a user.

Figure 5:
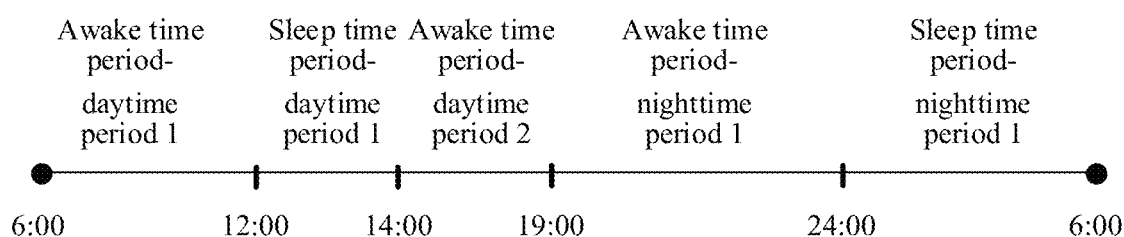
FIG. 5 is a schematic diagram of a time period division manner according to an embodiment of this application.

In some embodiments, the awake time period and the sleep time period each includes at least one first sub-period and/or second sub-period, the first sub-period is a daytime period, and the second sub-period is a nighttime period. In this embodiment of this application, a day is used as a basic unit, 24 hours in a day are divided into an awake time (awake time, AT) period and a sleep time (sleep time, ST) period, and the awake time period is further divided into at least one daytime (day time, DT) period and/or nighttime (night time, NT) period. FIG. 5 shows an example division manner. The awake time period includes a daytime period 1 that is from 6:00 to 12:00, a daytime period 2 that is from 14:00 to 19:00, and a nighttime period 1 that is from 19:00 to 24:00. The sleep time period includes a daytime time period 1 that is from 12:00 to 14:00 and a nighttime period 1 that is from 24:00 to 6:00.

Figure 6:
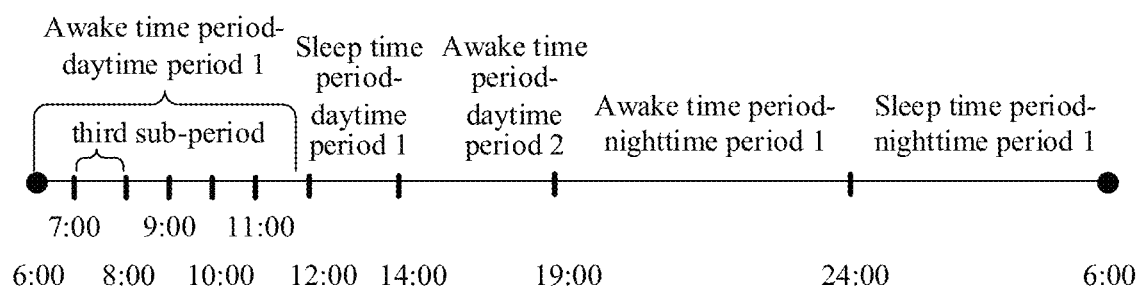
FIG. 6 is a schematic diagram of another time period division manner according to an embodiment of this application.

In some embodiments, to more precisely adjust an amount of light with improved real-time performance, the time period may be further divided by using a finer granularity. For example, as shown in FIG. 6, the daytime period 1 included in the awake time period in FIG. 5 is further divided into a plurality of third sub-periods at a finer granularity. For example, the daytime period 1 included in the awake time period in FIG. 5 is divided, at an interval of one hour, into six third sub-periods shown in FIG. 6. It may be understood that duration of the third sub-periods may be the same or different. This is not limited in this application.

Figure 7A:
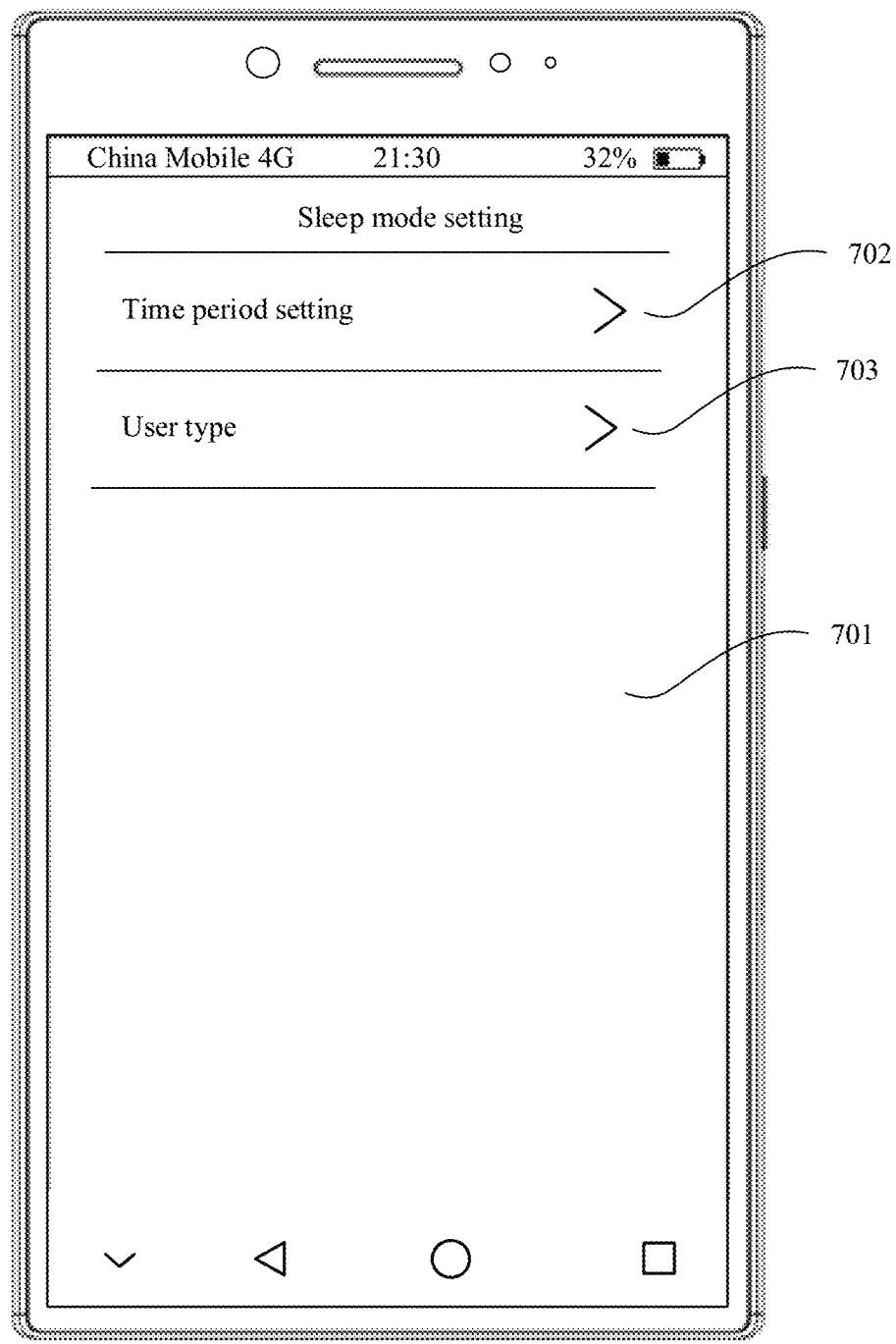
FIG. 7(a), FIG. 7(b), FIG. 7(c), and FIG. 7(d) are schematic diagram 1 of a scenario of a light adjustment method according to an embodiment of this application.
Figure 7B:
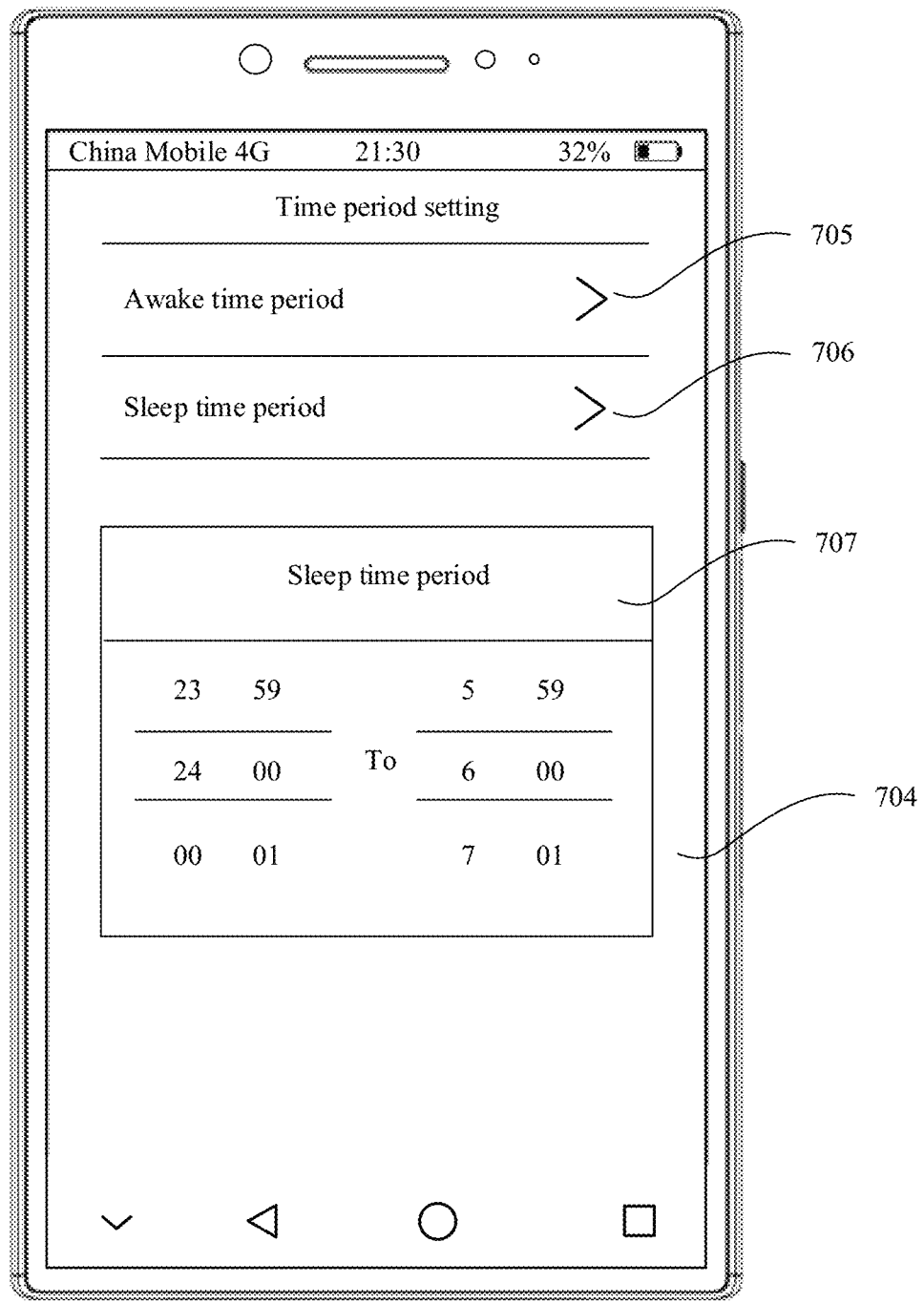

In this embodiment, the awake time period and the sleep time period may be determined in the following two manners:

Manner 1: The terminal receives time period division data entered by the user, and determines the awake time period and the sleep time period of the user based on the time period division data. As shown in FIG. 7(a), the terminal may provide a time period setting function item 702 in a sleep mode setting interface 701. The user may further set the awake time period and the sleep time period by using the time period setting function item 702. As shown in FIG. 7(b), in a time period setting interface 704, there is an awake time period setting item 705 and a sleep time period setting item 706. For example, the user taps the sleep time period setting item 706 to set a specific time of the sleep time period. For example, after the user taps the sleep time period setting item 706, the terminal pops up a sleep time period setting box 707 shown in FIG. 7(b), and the user sets the sleep time period to 24:00 to 6:00 in the sleep time period setting box 707.

For another example, the user may further set each first sub-period (daytime period) or second sub-period (nighttime period) in the awake time period by using the awake time period setting item 705. Specifically, after the user taps the awake time period setting item 705, the terminal makes a jump to an awake time period setting interface 708 shown in FIG. 7(c). The awake time period setting interface 708 includes a (first sub-period) daytime period setting item 709 and a (second sub-period) nighttime period setting item 710. The user may tap the daytime period setting item 709 to set the at least one daytime period included in the awake time period, and may further tap the nighttime period setting item 710 to set the at least one nighttime period included in the awake time period. For example, after the user taps the daytime period setting item 709, the terminal pops up a daytime period setting box 711 shown in FIG. 7(c), and the user sets the daytime period 1 included in the awake time period to 6:00 to 12:00.

Manner 2: The terminal obtains a first user profile of the user, and determines the awake time period and the sleep time period of the user based on the first user profile. The first user profile includes information such as a user behavior and a sleep status. The user behavior is a terminal-related behavior generated when the user uses the terminal. Behavior data is used to reflect the user behavior. The sleep status is used to describe sleep quality of the user, and sleep data is used to reflect the sleep status. The sleep data includes deep sleep duration, a deep sleep percentage (namely, a percentage of duration in which the user is in a deep sleep state in total sleep duration), a sleep score (namely, the sleep quality), and the like.

It should be noted that an actual user may be abstracted, based on a use behavior of the user, into a first user profile that includes one or more pieces of information. For example, a user A often watches an animation after 12:00 in the evening by using a mobile phone. In this case, information included in a first user profile obtained through abstraction is {sleep status: late sleep, user behavior: staying up late}. Table 1 shows a user profile of the user A that is in a form of a table. Information 1 (namely, sleep status information) indicates that a sleep status of the user A is late sleep, and information 2 (namely, user behavior information) indicates that a sleep behavior of the user A after 12:00 is staying up late. In addition, the user profile may be stored in a form of a configuration file (profile), a database, or the like.

TABLE 1

| User profile of the user A | |
| --- | --- |
| Information 1 | Sleep status: late sleep |
| Information 2 | User behavior: staying up late |

Figure 8A:
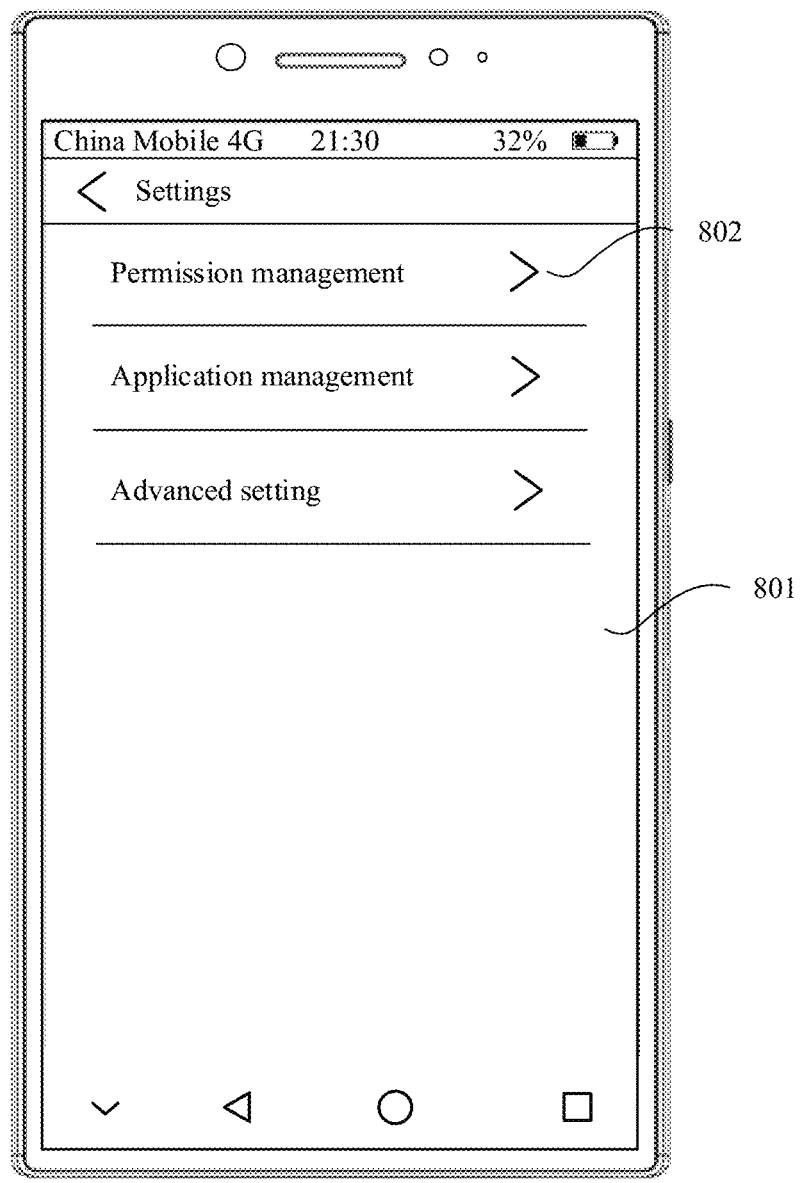
FIG. 8(a) and FIG. 8(b) are schematic diagram 2 of a scenario of a light adjustment method according to an embodiment of this application.
Figure 8B:
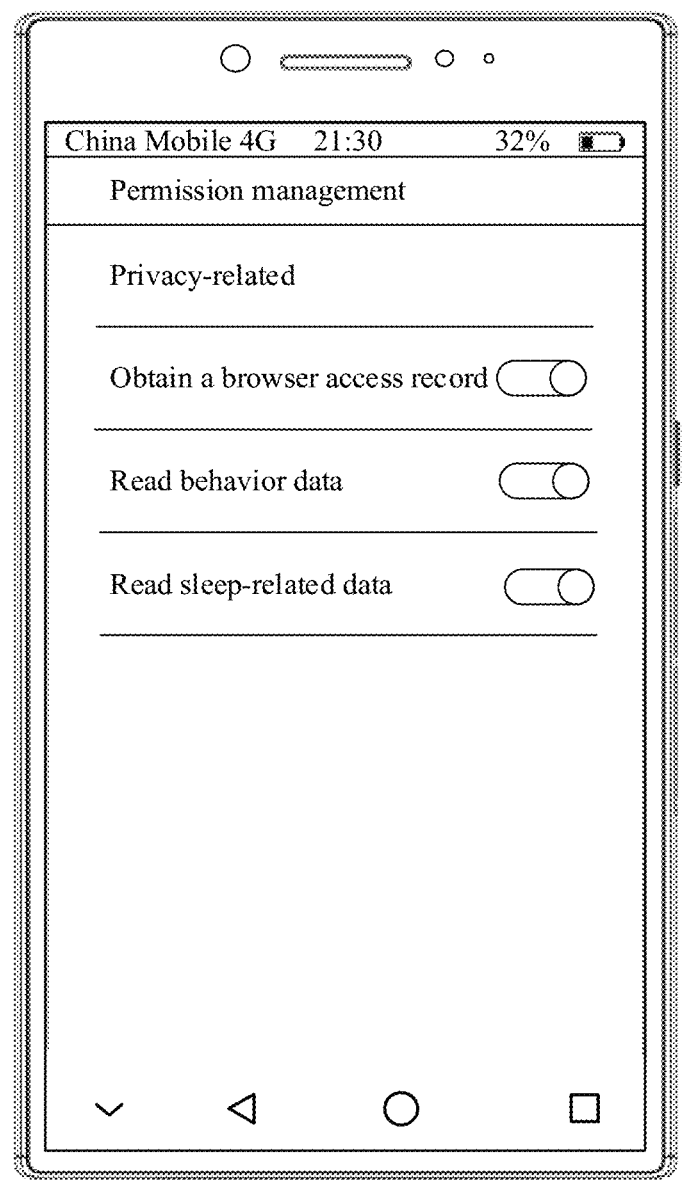

Herein, permission for the terminal to obtain the behavior data and/or the sleep data of the user may be enabled in advance. For example, the user enables the permission for the terminal by using a permission management setting item 802 in a setting interface 801 shown in FIG. 8(*a*) and FIG. 8(*b*). For example, the user enables permission to read the sleep data and permission to the read the behavior data.

For example, the first user profile includes the behavior data, and the behavior data represents that the user usually uses the terminal from 6:00 to 22:00. If the user has no habit of using the terminal from 22:00 to 6:00, the terminal may determine 6:00 to 22:00 as the awake time period of the user, and determine 22:00 to 6:00 as the sleep time period of the user.

For example, the first user profile includes the sleep data. The sleep data of the user may be obtained by using the wearable device (for example, the wristband) shown in FIG. 2, or the sleep data of the user may be obtained by using a device such as a smart mattress in a smart household scenario.

If the user has a relatively regular sleep cycle, in some embodiments, the terminal determines the time period based on average values of awake times and sleep times. A regular sleep cycle means a relatively fixed daily sleep time, fixed daily sleep duration, and the like. For example, the sleep data represents that the user usually goes to sleep (in other words, falls asleep) at 22:00 and usually wakes up (in other words, awakes) at 6:00. In this case, the terminal determines 22:00 to 6:00 as the sleep time period of the user, and determines 6:00 to 22:00 as the awake time period.

If the user has an irregular sleep cycle, in some embodiments, the terminal calculates medians, modes, and the like of awake times and sleep times, to determine the awake time period and the sleep time period.

If there is a relatively small amount of sleep data of the user, in some embodiments, an awake time and a sleep time in sleep data of the user in a particular day are randomly selected as a basis for determining the time period, or average values of a plurality of awake times and a plurality of sleep times in a preset quantity of pieces of sleep data are calculated, to determine the awake time period and the sleep time period.

In addition, a time period division manner corresponding to relatively good sleep quality may be determined as a current time period division manner. For example, after obtaining the sleep data of the user, the terminal determines that the sleep quality of the user is relatively good in the time period division manner shown in FIG. 6. In this case, the terminal uses the time period division manner shown in FIG. 6 as the current time period division manner.

Figure 9A:
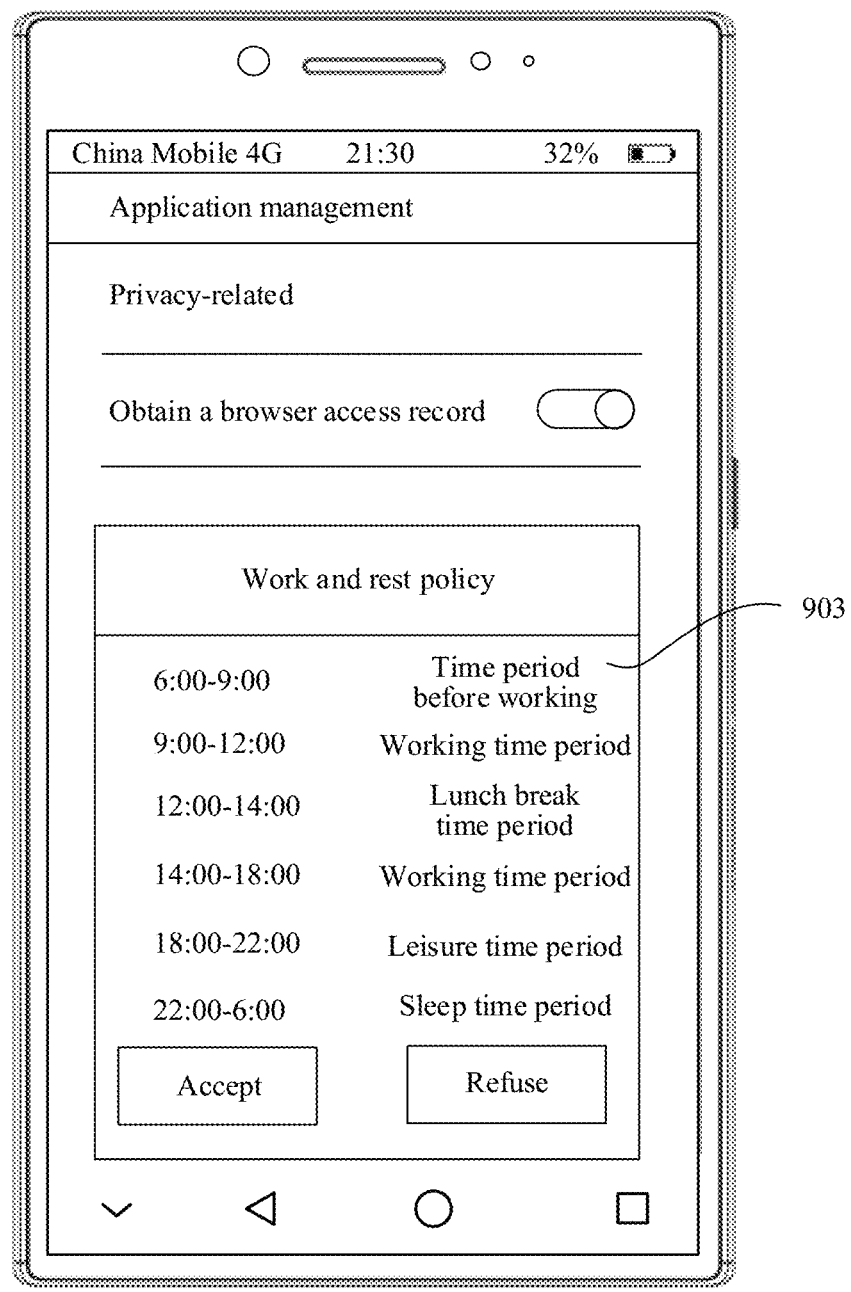
FIG. 9(a) and FIG. 9(b) are schematic diagram 3 of a scenario of a light adjustment method according to an embodiment of this application.
Figure 9B:
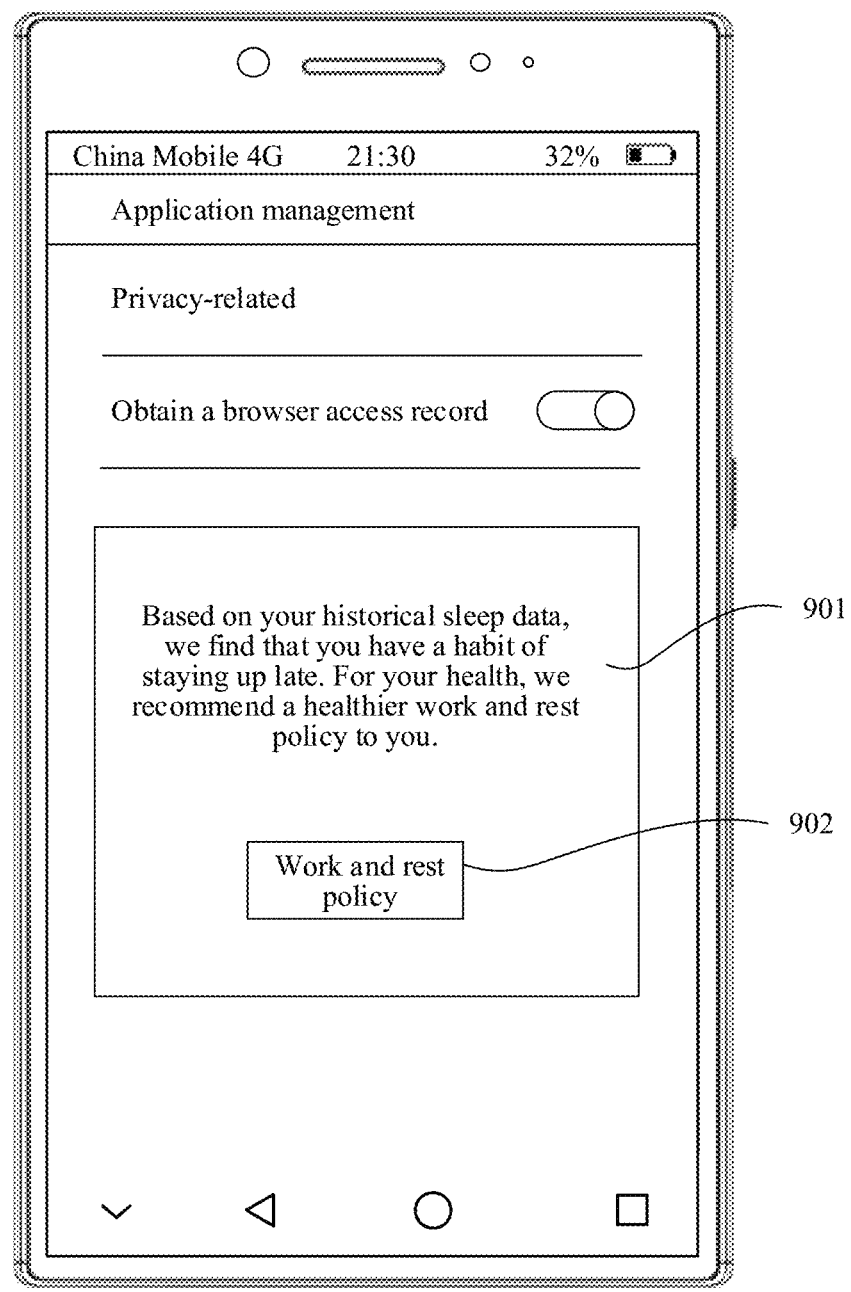

In addition, the terminal may recommend a time period division manner to the user. In a scenario, the terminal obtains the behavior data and the sleep data of the user. If it is determined that a work and rest pattern of the user belongs to a work and rest pattern indicating subhealth, a work and rest policy recommendation box 901 shown in FIG. 9(*a*) and FIG. 9(*b*) is displayed to prompt the user that the user may tap a work and rest policy item 902. After the terminal pops up a work and rest policy menu 903, the user may view a specific recommended work and rest policy.

S402. The terminal determines a light parameter threshold in each first sub-period and a light parameter threshold in each second sub-period.

A light parameter includes but is not limited to spectral distribution, light intensity, and an amount of light. The light parameter threshold includes a lower light parameter threshold and an upper light parameter threshold.

In some embodiments, the terminal determines the light parameter threshold in the following several manners:

Manner 1: The terminal calculates the light parameter threshold in each first sub-period and the light parameter threshold in each second sub-period. This manner may include the following several cases:

Case 1: The terminal obtains a second user profile of the user, and determines the light parameter threshold in each first sub-period and the light parameter threshold in each second sub-period based on the second user profile. Herein, a meaning of the second user profile is the same as that of the first user profile. A difference between the second user profile and the first user profile lies in that the second user profile and the first user profile include different information. The second user profile includes basic user information, a sleep status, a user behavior, and a user type. The basic information includes a gender, an age, an occupation, and the like of the user. For description of the user behavior and the sleep status, refer to the foregoing description. Details are not described herein again. The user type is used to reflect an individual feature of the user.

For example, the second user profile is the sleep status. In this case, the terminal determines the light parameter threshold in each first sub-period and the light parameter threshold in each second sub-period based on sleep data of the user. For description of the sleep data, refer to the foregoing description. Details are not described herein again.

For example, when the sleep data represents that the sleep quality of the user is relatively good, to balance a time ratio between work and sleep, a light parameter threshold in the awake time period may be appropriately increased under a condition that the sleep quality is not affected, to suppress melatonin secretion in the awake time period. This further improves working efficiency in the awake time period. For example, the light parameter is the light intensity. In an initial state, the light parameter threshold set by the terminal for the user in the awake time period is first light intensity. Subsequently, if the terminal detects that the sleep quality of the user is relatively good, the terminal may increase the light parameter threshold in the awake time period to second light intensity under a condition that the sleep quality of the user is not affected. In this way, the sleep quality of the user can be ensured and working efficiency of the user can be improved.

It should be noted that in this embodiment, secretion of melatonin is related to light at each moment. In addition, in consideration of an accumulative effect of light in a time period, the light parameter that affects the secretion of melatonin may alternatively be an accumulative amount of light (for ease of description, the accumulative amount of light is also referred to as an amount of light in this specification). Herein, the amount of light mainly indicates an amount of a target type of light. The target type of light is light related to regulation of a circadian rhythm. For detailed description, refer to the foregoing description. The amount of light may be calculated based on the light intensity and light duration. For example, if levels of light intensity at all moments in a time period are similar, that is, for any two moments in the time period, light intensity at a first moment is first light intensity, light intensity at a second moment is second light intensity, and a difference between the second light intensity and the first light intensity is less than a threshold, a product of average light intensity in the time period and duration is used as an amount of light in the time period. For another example, if light intensity changes greatly in a time period, the light intensity may be integrated in the time period by using a method such as an integral function, to obtain an amount of light in the time period.

In some embodiments, the amount of light is also related to spectral distribution.

Usually, a percentage of the target type of light in total light is higher. Therefore, a total amount of light in a time period may be calculated based on the spectral distribution, or a total amount of light in a time period may be calculated based on the spectral distribution, the light density, and the light duration. An example method for calculating a total amount of light may be determined based on an actual application situation. This is not limited in this embodiment of this application.

For example, the second user profile is the user behavior. In this case, the terminal obtains behaviors of the user in different daytime or nighttime periods, and determines a light parameter threshold in a current sub-period based on a behavior of the user in the current sub-period.

Figure 7C:
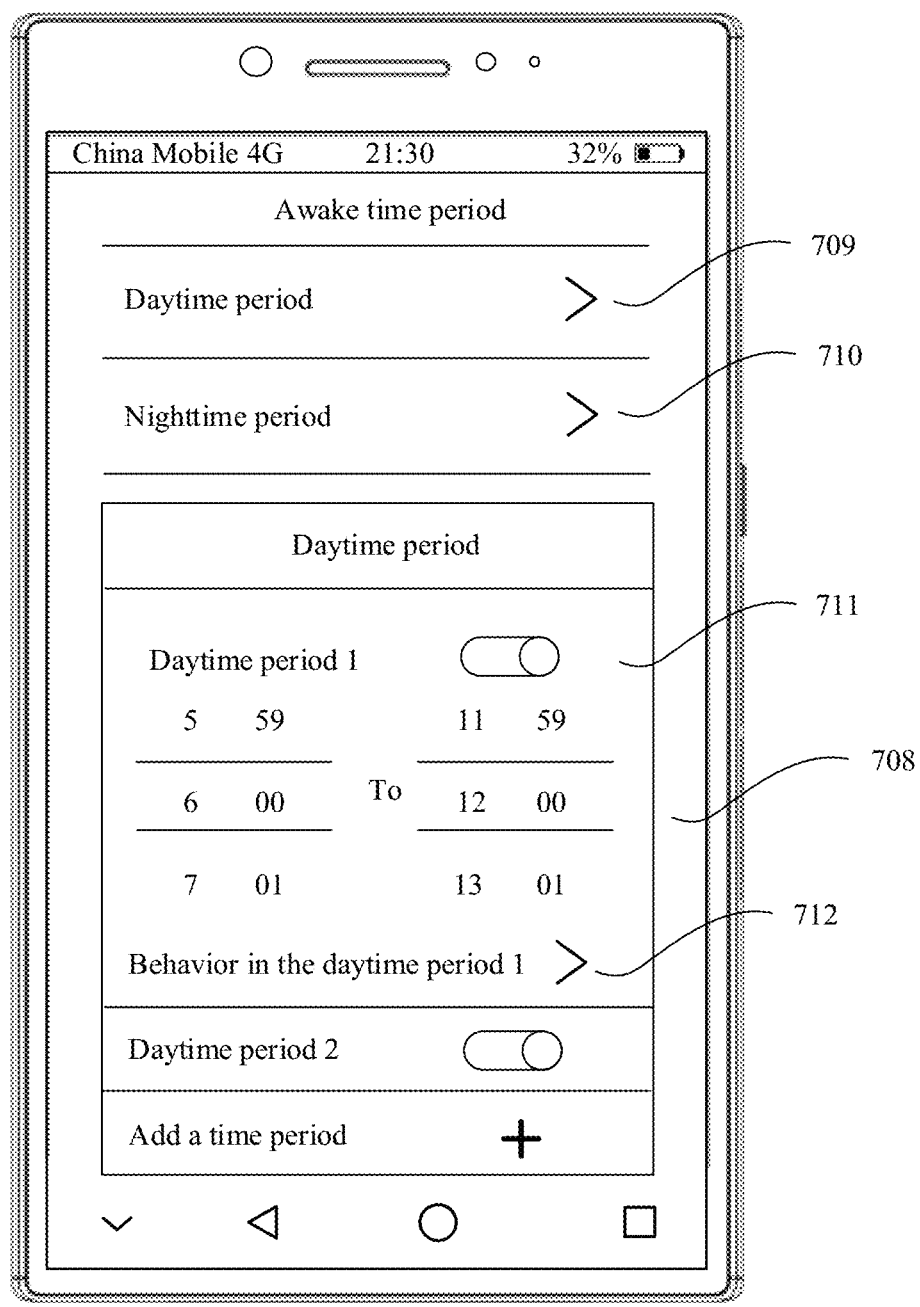
Figure 10:
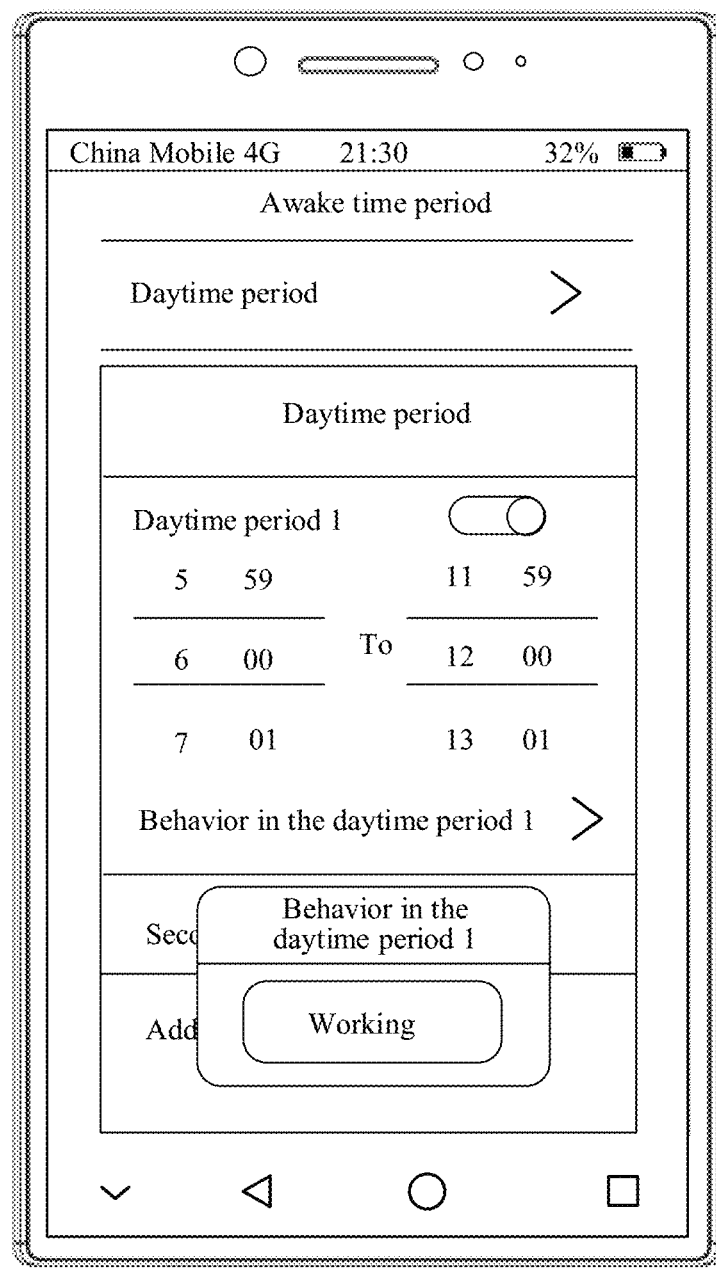
FIG. 10 is a schematic diagram 4 of a scenario of a light adjustment method according to an embodiment of this application.

In some embodiments, the user manually enters behaviors of the user in different daytime or nighttime periods. As shown in FIG. 7(c), a behavior setting item 712 of the daytime period 1 is set in the daytime period setting box 711. The user may set a behavior in the daytime period 1 by using the behavior setting item 712 of the daytime period 1. For example, the behavior in the daytime period 1 (6:00 to 12:00) is set to "working" shown in FIG. 10. Then, the terminal determines a light parameter threshold in each daytime period and a light parameter threshold in each nighttime period based on the behavior set by the user. In some embodiments, in a working time period, the light parameter threshold may be increased, and in a non-working time period (for example, a leisure time period), the light parameter threshold may be decreased.

Alternatively, the terminal collects the behavior data of the user, and determines behaviors of the user in different daytime nighttime periods based on an algorithm. For example, from 20:00 to 21:00, the behavior data represents that the user is playing a game. In this case, the terminal determines that the nighttime period is a leisure time period, and correspondingly sets a light parameter threshold for the leisure time period.

For example, the second user profile is the user type. In this case, the terminal determines a type of the terminal user, and sets different light parameter thresholds for different types of users.

Figure 7D:
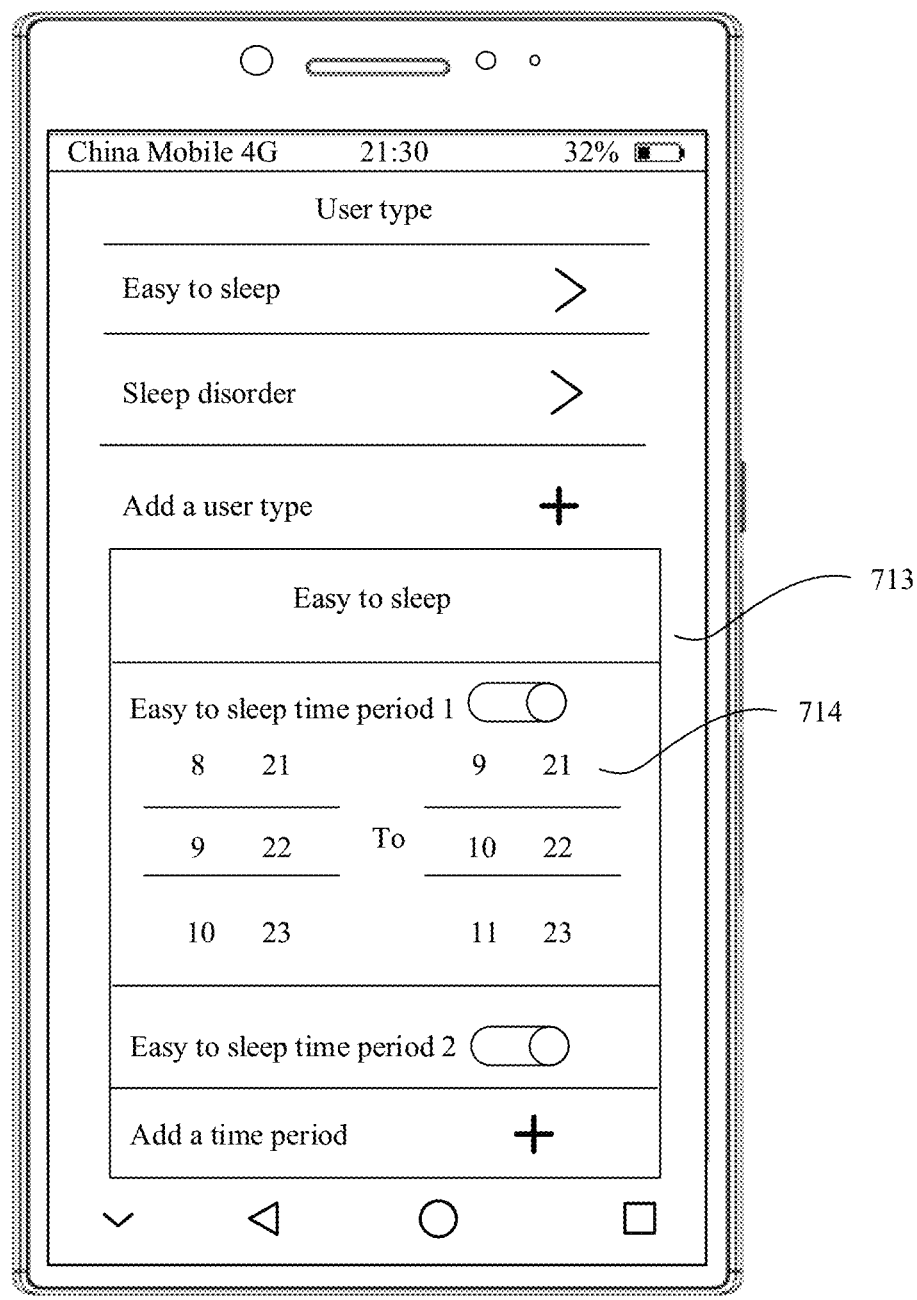

In some embodiments, the user manually sets the user type. As shown in FIG. 7(a), the user sets a specific user type by using a user type setting item 703. For example, in a user type setting interface 713 shown in FIG. 7(d), the user may select a user type included in the user type setting interface 713, for example, easy to sleep or sleep disorder. Alternatively, the user manually adds the user type. For example, after selecting the easy to sleep type, the user may set an easy to sleep time period in an easy to sleep setting window 714 popped up on the terminal.

Alternatively, the terminal collects the behavior data of the user, and determines the user type based on the behavior data of the user.

It may be understood that if the user is easy to sleep in a working time period, the terminal increases a light parameter threshold in the easy to sleep time period, to suppress melatonin secretion in the easy to sleep time period, and improve energy of the user. For a user with a sleep order, the terminal decreases a light parameter threshold of the user in a sleep latency. The sleep latency is a daytime period or a nighttime period that is included in the awake time period and that is before and adjacent to the sleep time period. For example, in the time period division manner shown in FIG. 6, in the daytime, the sleep latency is 11:00 to 12:00, and at night, the sleep latency is a preset time period that is before and adjacent to 24:00, for example, may be 23:00 to 24:00.

It may be learned that there are different light parameter thresholds for different types of users. The terminal flexibly adjusts a light parameter threshold in each daytime period and a light parameter threshold in each nighttime period based on a user requirement, to help the user improve a circadian rhythm, train a brain of the user, and develop a more appropriate work and rest pattern.

It should be understood that the foregoing merely lists several representation forms of the second user profile. In an actual application scenario, the second user profile may alternatively be in another representation form. This is not limited in this embodiment of this application.

Case 2: The terminal obtains geographical location information of the user, and determines the light parameter threshold in each first sub-period and the light parameter threshold in each second sub-period based on the geographical location information.

The geographical location information includes light intensity, a longitude and a latitude, a season, weather, sunrise and sunset times, and the like at a geographical location.

The light intensity is used as an example. When light intensity of natural light at the geographical location is relatively high, to ensure that the terminal is not triggered to adjust, when the user receives relatively strong natural light, a light parameter of light emitted by a light module 302, the light parameter threshold in each first sub-period and the light parameter threshold in each second sub-period should be increased. On the contrary, when light intensity of natural light at the geographical location is relatively low, the user receives relatively weak natural light, and correspondingly, the light parameter threshold in each first sub-period and the light parameter threshold in each second sub-period are decreased.

The geographical location information may alternatively be implemented in another form. This is not limited in this embodiment of this application.

Case 3: The light parameter threshold in each first sub-period and the light parameter threshold in each second sub-period are determined based on combination information of a second user profile and geographical location information of the user.

The geographical location information of the user and a user behavior in the second user profile are used as an example. The user settles in Beijing for a long time, and currently the user goes to Qinghai. Natural light intensity in Qinghai is greater than that in Beijing. It may be understood that when sleep quality statuses are similar, the user receives more light in Qinghai. Therefore, when the user is in Qinghai, the light parameter threshold in each first sub-period and the light parameter threshold in each second sub-period may be increased. In a possible implementation, when the user is in Qinghai and a time period is a working time period, a light parameter threshold in the working time period is increased.

In this embodiment, priorities of the geographical location and the user behavior may be further set. When the user is in Qinghai and a time period is a rest time period, if the priority of the geographical location is higher than the priority of the user behavior, a light parameter threshold in the rest time period is increased. On the contrary, if the priority of the geographical location is lower than the priority of the user behavior, a light parameter threshold in the rest time period is decreased. Alternatively, weights of the geographical location and the user behavior are set based on a degree to which the sleep quality is affected by the geographical location and the user behavior, and a light parameter threshold in the rest time period is determined based on the weights.

Manner 2: The terminal determines a target user, and respectively determines a light parameter threshold of the target user in each nighttime period and a light parameter threshold of the target user in each daytime period as the light parameter threshold in each first sub-period and the light parameter threshold in each second sub-period.

A user profile similarity between the target user and the user is greater than a threshold, and the user profile similarity is used to describe a similarity between second user profiles.

In some embodiments, example implementation of a manner of calculating the user profile similarity is: obtaining second user profiles of a first user and a second user, quantizing each piece of information included in the profile of the first user, quantizing each piece of information (for example, a sleep status and an occupation) included in the profile of the second user, and calculating a user profile similarity between the first user and the second user based on a quantization result. For example, an information eigenvalue of each piece of information is preset in the terminal. Herein, the information eigenvalue may reflect a sleep score. For example, a sleep moment 24:00 corresponds to an information eigenvalue of 60 (namely, 60 scores). A sleep moment 2:00 is later than the sleep moment 24:00, and an information eigenvalue corresponding to the sleep moment 2:00 may be 50 (namely, 50 scores, indicating that the sleep score is less than a sleep score of a user whose sleep moment is 24:00). Usually, a professional IT programmer sleeps later, and corresponds to an information eigenvalue of 50, and a professional white-collar worker sleeps earlier, and corresponds to an information eigenvalue of 80. A male sleeps later, and this piece of information corresponds to an information eigenvalue of 60, and gender information of a female corresponds to an information eigenvalue of 80.

If the second user profile of the first user includes the following information: male, a sleep moment 24:00, and an occupation of an information technology (Information Technology, IT) programmer, and the second user profile of the second user includes the following information: male, a sleep moment 2:00, and an occupation of an IT programmer. With reference to the information eigenvalue of each piece of information, an obtained quantization result of the second user profile of the first user may be as follows: {male: 60; sleep moment 24:00: 60; professional IT programmer: 50}, and an obtained quantization result of the second user profile of the second user may be as follows: {male: 60; sleep moment 2:00: 50; professional IT programmer: 50}. Herein, a weight may be assigned to each piece of information, to obtain a final quantization result. For example, a weight of gender information is 0.1, a weight of sleep time information is 0.6, and a weight of occupational information is 0.3. In this case, a final quantization result of the second user profile of the first user is 60*0.1+60*0.6+50*0.3=57, and a final quantization result of the second user profile of the second user is 60*0.1+50*0.6+50*0.3=51. If the user profile similarity is defined as a difference between quantization values of user profiles, the obtained user profile similarity is 57−51=6.

Herein, only an example of a manner of calculating the user profile similarity is provided. Certainly, the user profile similarity may be calculated by using a method such as a Euclidean distance method, a Manhattan distance method, an included angle cosine method, or a Pearson correlation coefficient method. For a process of calculating the user profile similarity by using another method, refer to the prior art. Details are not described in this application.

In some embodiments, the terminal obtains sleep data of another user from a server, where the terminal has permission to access the sleep data of the another user, and recommends, to the current user, a light parameter threshold corresponding to the target user with a similar geographical location, a similar second user profile, and relatively good sleep quality. For example, the current user is a male, is 33 years old, is an IT programmer, suffers from a sleep disorder, and lives in Xicheng District, Beijing. If the terminal determines, by accessing the server, that a user 1 has a same gender, age, and occupation as the target user (in other words, a second user profile of the user 1 is similar to that of the current user), and sleep quality of the user 1 is relatively good, the terminal determines the user 1 as the target user, and recommends the light parameter threshold of the target user in each daytime period and the light parameter threshold of the target user in each nighttime period to the current user, to determine the light parameter threshold of the current user in each first sub-period and the light parameter threshold of the current user in each sub-period.

Certainly, the target user may alternatively be a user with a relatively high profile similarity to the current user, a similar geographical location, and relatively good sleep quality. This is not limited in this embodiment of this application.

In some embodiments, the terminal may use a corresponding light parameter threshold obtained when the sleep quality of the current user is relatively good as a current light parameter threshold. For example, the terminal obtains the sleep data of the user, and determines that the user has best sleep quality on January 20 and that the user has a good health status on a date adjacent to January 20. In this case, the terminal respectively determines a light parameter threshold in each daytime period and a light parameter threshold in each nighttime period on January 20 as the light parameter threshold in each first sub-period and the light parameter threshold in each second sub-period on the current day.

According to the method for setting a light parameter threshold in this embodiment of this application, different light parameter thresholds mat be set based on different requirements of the user in different scenarios, and setting of the light parameter threshold is more suitable for an individual feature of the user and is more intelligent.

S403. The terminal determines whether the current sub-period is a nighttime period or a sleep time period, and performs S407 if the current sub-period is neither a nighttime period nor a sleep time period, or performs S404b if the current sub-period is a nighttime period, or performs S404a if the current sub-period is a sleep latency.

In the following embodiment, the light adjustment method in this embodiment described by using an example in which the terminal is a mobile phone.

S404a. The terminal adjusts a percentage of a target type of light in light emitted by a light source device to 0.

The target type of light is light related to regulation of a circadian rhythm. For example, the target type of light may be the foregoing ipRGC sensitive band light.

It may be understood that the ipRGC sensitive band light is closely related to melatonin secretion. If the current sub-period is a sleep latency, a percentage of the ipRGC sensitive band light is adjusted to 0, to reduce stimulation of the ipRGC sensitive band light on an eye of the user.

In some embodiments, in the sleep latency, the terminal may pop up a prompt box to prompt the user that "the current time period is a sleep latency (it is late), and please have a rest as soon as possible". After the user determines to accept the prompt, the terminal adjusts the percentage of the ipRGC sensitive band light to 0.

In addition, in the sleep latency, the terminal obtains the behavior data of the user. If the behavior data represents that the user is in a working state in the current sleep latency, the terminal may not adjust a light parameter of light emitted by the light source device. If the behavior data represents that the user is in a leisure state in the current sleep latency, the terminal may decrease the light parameter of the light emitted by the light source device, for example, decrease the percentage of the ipRGC sensitive band light in the light emitted by the light source device. Herein, the light source device may be the light module 302 in FIG. 3.

S404b. The terminal determines a total amount of light received in all daytime periods.

The time period division manner in FIG. 6 is used as an example. In this case, the total amount of light in the daytime periods is a total amount of light in a time period from 6:00 to 19:00.

S405. The terminal determines whether the amount of light received in the daytime periods exceeds a threshold range of the total amount of light in the daytime periods, and perform S407 if the amount of light received in the daytime periods does not exceed the threshold range of the total amount of light in the daytime periods, or performs S406a if the amount of light received in the daytime periods is greater than an upper threshold of the total amount of light in the daytime periods, or performs S406b if the amount of light received in the daytime periods is less than a lower threshold of the total amount of light in the daytime periods, or performs S406c if the amount of light received in the daytime periods is less than or equal to an upper threshold of the total amount of light in the daytime periods, and is greater than or equal to a lower threshold of the total amount of light in the daytime periods.

S406a. The terminal adjusts a light parameter of the light source device in each nighttime period to a third light parameter.

A third light parameter in a single nighttime period is less than a preset light parameter in the nighttime period.

It may be understood that the terminal determines, in a nighttime period that comes first in all nighttime periods (for example, the nighttime period 1 included in the awake time period in FIG. 6), the total amount of light received in the daytime periods. When the total amount of light received in the daytime periods is greater than the upper threshold of the total amount of light in the daytime periods, the user receives a relatively large amount of light in the daytime periods, and a little amount of melatonin is secreted. In this case, the user has relatively high working efficiency in the daytime, and the user is relatively tired. To prevent the user from being overly tired, a light parameter threshold in each nighttime period may be decreased, so that the user receives a relatively small amount of light in each nighttime period, to lessen fatigue of the user, and make a preparation for the user to sleep. For example, a preset light parameter 1 is initially set for the nighttime period 1, and a preset light parameter 2 is initially set for the nighttime period 2. When it is detected that the total amount of light received by the user in the daytime periods is greater than the threshold of the total amount of light in the daytime periods, a light parameter in the nighttime period 1 is adjusted from the preset light parameter 1 to a third light parameter 1, and a light parameter in the nighttime period 2 is adjusted from the preset light parameter 2 to a third light parameter 2. The third light parameter 1 is less than the preset light parameter 1, and the third light parameter 2 is less than the preset light parameter 2. The preset parameter 1 may be the same as or different from the preset parameter 2. Similarly, the third light parameter 1 may be the same as or different from the third light parameter 2.

In some embodiments, light parameters only in some nighttime sub-periods may be adjusted. For example, the preset light parameter 1 is adjusted to the third light parameter 1, or only the preset light parameter 2 is adjusted to the third light parameter 2. This is not limited in this embodiment of this application.

S406b. The terminal adjusts a light parameter of the light source device in each nighttime period to a fourth light parameter.

A fourth light parameter in a single nighttime period is greater than a preset light parameter in the single nighttime period.

When the total amount of light received in the daytime periods is less than the lower threshold of the total amount of light in the daytime periods, the user receives a relatively small amount of light in the daytime, and a relatively large amount of melatonin is secreted. This may result in lower working efficiency of the user in the daytime. Therefore, it is considered to do part of work at night. In this case, a light parameter threshold in each nighttime period may be increased, so that the user receives a relatively large amount of light in the nighttime period, to improve working energy.

It may be understood that when the total amount of light received in the daytime periods is less than the lower threshold of the total amount of light in the daytime periods, the light parameter threshold in each nighttime period may not be adjusted, that is, light with relatively weak light intensity or light in which a percentage of the ipRGC sensitive band light is relatively low in the nighttime period is still maintained, so that the user can quickly sleep.

S406c. The terminal maintains a preset light parameter in a nighttime sub-period.

If the terminal determines that a total amount of light received in all daytime sub-periods is greater than or equal to a lower threshold of the total amount of light in the daytime sub-periods, and is less than or equal to an upper threshold of the total amount of light in the daytime sub-periods, it indicates that the total amount of light received by the user in the daytime sub-periods meets a user requirement, and the amount of light received by the user does not need to be adjusted by using the light source device. In this case, the terminal maintains the preset light parameter in the nighttime sub-period.

S407. The terminal obtains a light parameter in the current sub-period.

The light parameter includes but is not limited to light intensity, spectral distribution, and an amount of light.

In this embodiment, if the current sub-period is a nighttime period, the terminal may perform the foregoing procedure of adjusting the light parameter threshold in each nighttime period, and determine the light parameter in the current sub-period (nighttime period) after adjusting the light parameter threshold in the nighttime period.

If the current sub-period is neither a nighttime period nor a sleep latency, the terminal obtains the light parameter in the current sub-period.

In this embodiment of this application, there may be the following two scenarios in which the terminal obtains the light parameter:

Scenario 1: When the user holds the mobile phone, light received by the mobile phone may be used as light received by the user. For example, the light parameter is the light intensity and the spectral distribution. In this case, S407 may be implemented as follows: A light sensing module 307 in the terminal may directly detect and obtain light intensity of the light received by the terminal and a percentage of the ipRGC sensitive band light. For example, the light parameter is the amount of light. In this case, S407 may be implemented as follows: A light sensing module 307 in the terminal may directly detect and obtain light intensity of the light received by the terminal and a percentage of the ipRGC sensitive band light, and transfer the obtained light intensity to the processor 301 shown in FIG. 3. The processor 301 calculates an amount of light in the current sub-period based on the light intensity in the current sub-period. For example, the amount of light is a product of the light intensity and duration of the current sub-period. Herein, it is assumed that the light intensity in the current sub-period is a constant value. In practice, the light intensity may be different at each moment in the current sub-period. In this case, the processor 301 may calculate the amount of light in the current sub-period based on a specific algorithm. This is not limited in this application.

In some embodiments, to more precisely calculate an amount of light received by the user, the terminal may map an amount of light received by the terminal to the amount of light received by the user. In some embodiments, an effective amount of light received by the user when the terminal receives a specific amount of light is determined by using big data analysis or an artificial intelligence algorithm. For specific processing of the big data analysis or the artificial intelligence algorithm, refer to the prior art. Details are not described herein.

Scenario 2: When the mobile phone is placed in a bag by the user, a light sensing module 307 is at a light shielding position, and a light parameter detected by the light sensing module 307 cannot reflect a light parameter of light received by the user. Alternatively, it is set that a light sensing function of the mobile phone is disabled, and the mobile phone cannot detect a light parameter of received light. In these scenarios, there may be the following two manners of obtaining the light parameter of the light received by the user in the current sub-period:

Manner 1: The terminal obtains the light parameter from another terminal. For example, the terminal sends a light parameter obtaining instruction to the another terminal (for example, a wearable device worn by the user), to obtain the light parameter detected by the another terminal. The wearable device is usually worn by the user and is usually not at a light shielding position, and therefore the light parameter detected by the wearable device may be used to reflect the light parameter of the light received by the user. In this way, the mobile phone can still obtain, when the mobile phone is at the light shielding position, the light parameter of the light received by the user.

It should be noted that the light parameter of the light received by the terminal changes with an affecting factor. Different light parameters may be obtained in a case of different affecting factors, and similar light parameters are usually obtained in a case of similar affecting factors. The affecting factors include but are not limited to a season, weather, and a geographical location (altitude). For example, in a same region, there are usually different light parameters in spring and summer. For another example, in a same region, in sunny spring days with a temperature of 21° C. and a force 3 wind, daily light parameters from 9:00 a.m. to 12:00 a.m. are usually similar. Based on this, when the mobile phone is in a light shielding scenario, the following manner of obtaining the light parameter of the light received by the user is provided:

Manner 2: A light parameter under a condition of a similar affecting factor is used as the light parameter in the current sub-period. Specifically, the mobile phone sends a light parameter under a preset condition to the server based on a preset period. The preset condition includes a weather condition and geographical location information. Herein, the weather condition includes windy, sunny, rainy, snowy, a temperature, air humidity, air quality (including a pollution index), wind force, a wind direction, and the like. Then, the server analyzes and processes the light parameter sent by the mobile phone. Subsequently, when the user does not wear the wearable device or the like and the mobile phone is at the light shielding position, or when the user wears the wearable device and both the wearable device and the mobile phone are at the light shielding position, the mobile phone may obtain, from the server, a light parameter obtained at a current geographical location and in a current weather condition. For example, the preset period is set to an hour, and the mobile phone sends a light parameter in a current one-hour time period to the server every hour. At a start moment of an hour, a light parameter 1 sent by the mobile phone to the server is as follows: {light intensity 1000 lux; weather: sunny; temperature: 18° C.; air humidity: 21%; air quality (including a pollution index): 61, good; wind force: southwest wind; wind direction: force 3 to 4; geographical location: Xicheng District, Beijing}. At a start moment of a next hour, a light parameter 2 sent by the mobile phone to the server is as follows: {light intensity: 500 lux; weather: cloudy; temperature: 17° C.; air humidity: 19%; air quality: 64, good; wind force: southwest wind; wind direction: force 3 to 4; geographical location: Xicheng District, Beijing}. By analogy, the mobile phone or the wearable device sends the light parameter in each daytime period and the light parameter in each nighttime period to the server. Subsequently, when it is inconvenient for the user to collect a current light parameter by using the mobile phone, the wearable device, or the like, the mobile phone or the wearable device obtains a current geographical location of the user and a weather condition, and obtains a light parameter under a similar weather condition and/or a similar geographical location condition from the server. For example, the current geographical location of the user and the weather condition that are obtained by the mobile phone, the wearable device, or the like are as follows: {weather: sunny; temperature: 19° C.; air humidity: 21%; air quality: 61, good; wind force: southwest wind; wind direction: force 3 to 4; geographical location: Xicheng District, Beijing}. The current geographical location of the user and the weather condition are sent to the server. The server queries a stored light parameter, and determines that the geographical location and the weather condition corresponding to the light parameter 1 are most similar to the current geographical location of the user and the weather condition. In this case, the server uses the light parameter 1 as the light parameter in the current sub-period. Certainly, in addition to the foregoing factors such as the season, the weather, and the geographical location that affect the light parameter, there may be another factor that affects the light parameter. This is not limited in this embodiment of this application.

S408. The terminal adjusts, based on the light parameter in the current sub-period, a light parameter of light emitted by the light source device in a next sub-period of the current sub-period.

In some embodiments, the terminal compares the light parameter in the current sub-period with a light parameter threshold in the current sub-period, to determine how to adjust the light parameter of the light emitted by the light source device.

In a first case, if the terminal determines, through comparison, that the light parameter of the light received by the user in the current sub-period is less than a lower light parameter threshold in the current sub-period, it indicates that the user receives a relatively small amount of light in the current sub-period, and a requirement of the user for a large amount of light cannot be met (for example, melatonin secretion cannot be suppressed). In this case, the processor 301 in the terminal adjusts the light parameter of the light emitted by the light source device in the next sub-period of the current sub-period to a first light parameter. The first light parameter is greater than the light parameter in the current sub-period. In some embodiments, in visible light, the ipRGC sensitive band light is main response light of an ipRGC. Therefore, the processor 301 increases the percentage of the ipRGC sensitive band light in the total light. Alternatively, the processor 301 increases overall light intensity. Alternatively, after the percentage of the ipRGC sensitive band light in the total light is adjusted, a color of the total light may change. To prevent the user from perceiving a change of the light, the processor 301 further adjusts intensity of light other than the ipRGC sensitive band light, that is, adjusts spectral distribution (a percentage of each type of light in a spectrum), so that the color of the total light irradiated into the eye of the user does not change greatly.

It should be noted that blue light may damage an eye ground and a retina. Therefore, when adjusting the light module 302, the processor 301 may decrease a percentage of the blue light or shield the blue light.

In a second case, if the processor 301 determines, through comparison, that the light parameter of the light received by the user in the current sub-period is greater than an upper light parameter threshold in the current sub-period, it indicates that there is a relatively large amount of light in the current sub-period, and fatigue is easily caused. In this case, the processor 301 adjusts the light parameter of the light emitted by the light source device in the next sub-period of the current sub-period to a second light parameter. The second light parameter is less than the light parameter in the current sub-period.

In a third case, if the processor 301 determines, through comparison, that the light parameter in the current sub-period is less than or equal to an upper light parameter threshold in the current sub-period, and is greater than or equal to a lower light parameter threshold in the current sub-period, it indicates that light in the current sub-period meets a user requirement. In this case, the processor 301 does not instruct to adjust the light module 302. In this way, in irradiation of natural light, a melatonin secretion status of the user still meets a rhythm requirement of the user.

In comparison with the prior art in which light and an amount of light provided by a light therapy device cannot better meet a user requirement, and cannot more intelligently improve sleep quality of a user, in the light adjustment method provided in this embodiment of this application, the terminal determines the awake time period and the sleep time period of the user; determines the light parameter threshold in each first sub-period and the light parameter threshold in each second sub-period. obtains the light parameter of the light received by the user in the current sub-period; and adjusts the light parameter of the light emitted by the light source device in the next sub-period of the current sub-period based on the light parameter of the light actually received by the user in the current sub-period and the light parameter threshold in the current sub-period. In this way, light received by the user in each sub-period better meets a user requirement, and therefore sleep quality of the user can be more intelligently improved.

In this embodiment, the light parameter adjustment procedure may alternatively be performed only in one time period. For example, if the user makes a setting to perform the light adjustment procedure from 9:00 to 11:00, the terminal detects, only in the time period, the light parameter of the light received by the user, and adjusts, based on the light parameter, the light parameter of the light received by the user.

In addition, in this embodiment, a terminal that provides a better light parameter adjustment effect may be intelligently selected through interaction between a plurality of terminals, to perform the light parameter adjustment procedure. Specifically, the terminal sends a light adjustment instruction to a target terminal, to instruct the target terminal to perform the light parameter adjustment procedure. For example, for a worker who usually sits in an office and faces a large-screen terminal (for example, a computer), the large-screen terminal may perform the procedure of adjusting the light parameter of the light emitted by the screen. A light parameter adjustment effect is more significant because of a relatively large screen area of the large-screen terminal.

In some embodiments, the mobile phone detects whether a face of the user is in front of a screen. If the face of the user is in front of the screen, the mobile phone continues to perform the light parameter adjustment procedure. If the face of the user is not in front of the screen, the mobile phone instructs the large-screen terminal (the face of the user is currently in front of the large-screen terminal) to perform the light parameter adjustment procedure. Certainly, in a scenario in which the mobile phone detects that the face of the user is in front of the screen, to improve a light parameter adjustment effect, the mobile phone may instruct the large-screen terminal to adjust a light parameter related to melatonin secretion for the user.

It may be understood that to implement the foregoing functions, the terminal includes a corresponding hardware structure and/or software module for performing each of the functions. With reference to the units and algorithm steps described in the embodiments disclosed in this application, embodiments of this application can be implemented in a form of hardware or hardware and computer software. Whether a function is performed by hardware or hardware driven by computer software depends on particular applications and design constraints of the technical solutions. A person skilled in the art may use different methods to implement the described functions for each particular application, but it should not be considered that the implementation falls beyond the scope of the technical solutions in the embodiments of this application.

In the embodiments in accordance with the disclosure, function unit division may be performed on the terminal based on the foregoing method examples. For example, each function unit may be obtained through division based on a corresponding function, or two or more functions may be integrated into one processing unit. The integrated unit may be implemented in a form of hardware, or may be implemented in a form of a software functional unit. It should be noted that, in this embodiment of this application, unit division is exemplary, and is merely a logical function division. In actual implementation, another division manner may be used.

Figure 11:
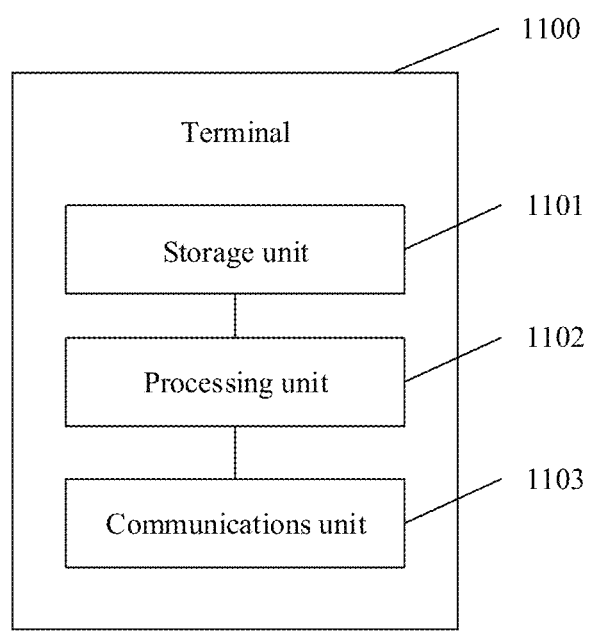
FIG. 11 is a schematic structural diagram of a terminal according to an embodiment of this application.

FIG. 11 is a schematic block diagram of a terminal according to an embodiment of this application. The terminal 1100 may be in a form of software, or may be a chip that can be used for a terminal. The terminal 1100 includes a processing unit 1102 and a communications unit 1103. For example, the processing unit 1102 may be configured to support the terminal 1100 in performing S401 and S402 in FIG. 4A and FIG. 4B, and/or another process in the solution described in this specification. The communications unit 1103 is configured to support the terminal 1100 in communicating with another network element (for example, the server 21 in FIG. 2 or another terminal).

In some embodiments, the terminal 1100 may further include a storage unit 1101, configured to store program code and data of the terminal 1100. The data may include but is not limited to raw data or intermediate data.

The processing unit 1102 may be a processor or a controller, such as may be a central processing unit (CPU), a general-purpose processor, a digital signal processor (DSP), an application-specific integrated circuit (ASIC), a field programmable gate array (FPGA), or another programmable logical device, a transistor logical device, a hardware component, or any combination thereof. The processor may implement or execute various example logical blocks, modules, and circuits described with reference to content disclosed in this application. The processor may be a combination of processors implementing a computing function, for example, a combination of one or more microprocessors, or a combination of the DSP and a microprocessor. The communications unit 1103 may be a transceiver, a transceiver circuit, the communications interface 308 shown in FIG. 3, or the like. The storage unit 1101 may be the memory 303 shown in FIG. 3.

A person of ordinary skill in the art may understand that all or some of the foregoing embodiments may be implemented by using software, hardware, firmware, or any combination thereof. When software is used to implement the embodiments, the embodiments may be implemented completely or partially in a form of a computer program product. The computer program product includes one or more computer instructions. When the computer program instructions are loaded and executed on the computer, the procedure or functions according to the embodiments of this application are all or partially generated. The computer may be a general-purpose computer, a dedicated computer, a computer network, or other programmable apparatuses. The computer instructions may be stored in a computer-readable storage medium or may be transmitted from a computer-readable storage medium to another computer-readable storage medium. For example, the computer instructions may be transmitted from a website, computer, server, or data center to another website, computer, server, or data center in a wired (for example, a coaxial cable, an optical fiber, or a digital subscriber line (DSL)) or wireless (for example, infrared, radio, or microwave) manner. The computer-readable storage medium may be any usable medium accessible by a computer, or a data storage device, such as a server or a data center, integrating one or more usable media. The usable medium may be a magnetic medium (for example, a floppy disk, a hard disk, or a magnetic tape), an optical medium (for example, a digital video disc (Digital Video Disc, DVD)), a semiconductor medium (for example, a solid-state drive (Solid State Disk, SSD)), or the like.

In the several embodiments herein it should be understood that the disclosed system, apparatus, and method may be implemented in other manners. For example, the described apparatus embodiment is merely an example. For example, the unit division is merely logical function division and may be other division in actual implementation. For example, a plurality of units or components may be combined or integrated into another system, or some features may be ignored or not performed. In addition, the displayed or discussed mutual couplings or direct couplings or communication connections may be implemented through some interfaces. The indirect couplings or communication connections between the apparatuses or units may be implemented in electronic or other forms.

The units described as separate parts may or may not be physically separate, and parts displayed as units may or may not be physical units, may be located in one position, or may be distributed on a plurality of network device (for example, a terminal). Some or all of the units may be selected based on actual requirements to achieve the objectives of the solutions of the embodiments.

In addition, functional units in the embodiments of this application may be integrated into one processing unit, or each of the functional units may exist independently, or two or more units are integrated into one unit. The integrated unit may be implemented in a form of hardware, or may be implemented in a form of hardware in addition to a software functional unit.

Based on the foregoing descriptions of the implementation manners, a person skilled in the art may clearly understand that this application may be implemented by software in addition to necessary universal hardware or by hardware only. In most circumstances, the former is a preferred implementation manner. Based on such an understanding, the technical solutions of this application essentially or the part contributing to the prior art may be implemented in a form of a software product. The software product is stored in a readable storage medium, such as a floppy disk, a hard disk or an optical disc of a computer, and includes several instructions for instructing a computer device (which may be a personal computer, a server, or a network device) to perform the methods described in the embodiments of this application.

The foregoing descriptions are merely specific implementations of this application, but are not intended to limit the protection scope of this application. Any variation or replacement within the technical scope disclosed in this application shall fall within the protection scope of this application. Therefore, the protection scope of this application shall be subject to the protection scope of the claims.

What is claimed is:

1. A light adjustment method being implemented electronically by a terminal, the light adjustment method comprising:
    determining, by the terminal, an awake time period and a sleep time period of a user, wherein the awake time period and the sleep time period each include at least a first sub-period and/or a second sub-period;
    determining, by the terminal, light parameter thresholds in a current time period, wherein the current time period is the awake time period or the sleep time period;

obtaining, by the terminal, a light parameter in the current time period; and adjusting, by the terminal based on the light parameter and the light parameter thresholds in the current time period, a light parameter of light emitted by a light source device, wherein the light parameter thresholds include a lower light parameter threshold and an upper light parameter threshold, and adjusting the light parameter of light emitted by the light source device comprises:

if a light parameter in a current sub-period is less than the lower light parameter threshold in the current sub-period, adjusting, by the terminal, the light parameter of light emitted by the light source device, in a next sub-period of the current sub-period, to a first light parameter, wherein the current sub-period includes the first sub-period or the second sub-period, and the first light parameter is greater than the light parameter in the current sub-period; and if a light parameter in a current sub-period is greater than the upper light parameter threshold in the current sub-period, adjusting, by the terminal, the light parameter of light emitted by the light source device, in a next sub-period of the current sub-period, to a second light parameter, wherein the second light parameter is less than the light parameter in the current sub-period, wherein the light adjustment method regulates the circadian rhythm of the user; and the terminal has a light detection function, and the light source device is configured for disposal inside the terminal or configured as an independent device communicating with the terminal.

2. The method according to claim 1, wherein
the first sub-period includes a daytime period, and the second sub-period includes a nighttime period.

3. The method according to claim 2, wherein the determining the awake time period and the sleep time period of the user comprises at least one of:

receiving, by the terminal, time period division data entered by the user, and determining, by the terminal, the awake time period and the sleep time period of the user based on the time period division data; or obtaining, by the terminal, a first user profile of the user, wherein the first user profile includes a user behavior and a sleep status, and the sleep status is associated with sleep quality of the user, and determining, by the terminal, the awake time period and the sleep time period of the user based on the first user profile.

4. The method according to claim 3, wherein the determining, by the terminal, the light parameter thresholds in the current time period comprises:

obtaining, by the terminal, a second user profile and/or geographical location information of the user; and determining, by the terminal, a light parameter threshold in each of the first sub-period and a light parameter threshold in each of the second sub-period based on the second user profile and/or the geographical location information of the user.

5. The method according to claim 3, wherein the determining, by the terminal, the light parameter thresholds in the current time period comprises:

if a user profile similarity between a target user and the user is greater than a threshold, respectively determining, by the terminal, a light parameter threshold of the target user in each daytime period and a light parameter threshold of the target user in each nighttime period as a light parameter threshold in each of the first sub-period and a light parameter threshold in each of the second sub-period, wherein the user profile similarity indicates a similarity between second user profiles.

6. The method according to claim 1, wherein after determining, by the terminal, the light parameter thresholds in the current time period, the method further comprises:

determining, by the terminal, a total amount of light received in all daytime periods;

if the total amount of light received in all the daytime periods is greater than an upper threshold of a total amount of light in the daytime periods, adjusting, by the terminal, a light parameter of the light source device in a nighttime period to a third light parameter, wherein the third light parameter in a single nighttime period is less than a preset light parameter in the single nighttime period; and if the total amount of light received in all the daytime periods is less than a lower threshold of the total amount of light in the daytime periods, adjusting, by the terminal, a light parameter of the light source device in a nighttime period to a fourth light parameter, wherein the fourth light parameter in a single nighttime period is greater than a preset light parameter in the single nighttime period.

7. The method according to claim 6, wherein after determining, by the terminal, the light parameter thresholds in the current time period, the method further comprises:

if the current sub-period includes a sleep latency, adjusting, by the terminal, a percentage of a target type of light emitted by the light source device to 0, wherein the target type of light relates to the regulation of the circadian rhythm, and the sleep latency is the first sub-period or the second sub-period comprised in the awake time period and before and adjacent to the sleep time period.

8. The method according to claim 7, wherein the adjusting, by the terminal, the light parameter of light emitted by the light source device comprises:

sending, by the terminal, a light adjustment instruction to a target terminal, wherein the light adjustment instruction instructs the target terminal to adjust the light parameter of the light emitted by the light source device.

9. A terminal, comprising:
a processor; and
a memory configured to store computer readable instructions that, when executed by the processor, cause the processor to:

determine an awake time period and a sleep time period of a user, wherein the awake time period and the sleep time period each include at least a first sub-period and/or a second sub-period;

determine light parameter thresholds in the awake time period and the sleep time period;

obtain a light parameter in a current time period, wherein the current time period includes the awake time period or the sleep time period; and adjust, based on the light parameter and the light parameter thresholds in the current time period, a light parameter of light emitted by a light source device, wherein the light parameter thresholds include a lower light parameter threshold and an upper light parameter threshold, and adjusting the light parameter of light emitted by the light source device comprises:
if a light parameter in a current sub-period is less than the lower light parameter threshold in the current sub-period, adjusting, by the terminal, the light parameter of light emitted by the light source device, in a next sub-period of the current sub-period, to a first light parameter, wherein the current sub-period includes the first sub-period or the second sub-period, and the first light parameter is greater than the light parameter in the current sub-period; and
if a light parameter in a current sub-period is greater than the upper light parameter threshold in the current sub-period, adjusting, by the terminal, the light parameter of light emitted by the light source device, in a next sub-period of the current sub-period, to a second light parameter, wherein the second light parameter is less than the light parameter in the current sub-period, wherein
the terminal regulates the circadian rhythm of the user by adjusting the light parameter of light emitted by the light source device; and
the light source device is configured for disposal inside the terminal or configured as an independent device communicating with the terminal.

10. The terminal according to claim 9, wherein the first sub-period includes a daytime period, and the second sub-period includes a nighttime period.

11. The terminal according to claim 10, wherein
the determining the awake time period and the sleep time period of the user comprises at least one of:
receiving time period division data entered by the user, and determining the awake time period and the sleep time period of the user based on the time period division data; or
obtaining a first user profile of the user, wherein the first user profile includes a user behavior and a sleep status, and the sleep status indicates sleep quality of the user, and determining the awake time period and the sleep time period of the user based on the first user profile.

12. The terminal according to claim 11, wherein
the processor is further caused to:
obtain a second user profile and/or geographical location information of the user, and determine the light parameter threshold in each of the first sub-period and the light parameter threshold in each of the second sub-period based on the second user profile and/or the geographical location information of the user.

13. The terminal according to claim 11, wherein
the processor is further caused to:
respectively determine a light parameter threshold of a target user in each daytime period and a light parameter threshold of the target user in each nighttime period as a light parameter threshold in each of the first sub-period and a light parameter threshold in each of the second sub-period if a user profile similarity between a target user and the user is greater than a threshold, wherein the user profile similarity indicates a similarity between second user profiles.

14. The terminal according to claim 9, wherein
after determining the light parameter thresholds in the awake time period and the sleep time period, the processor is further caused to:
determine a total amount of light received in all daytime periods, and adjust a light parameter of the light source device in a nighttime period to a third light parameter if the total amount of light received in all the daytime periods is greater than an upper threshold of a total amount of light in the daytime periods, wherein the third light parameter in a single nighttime period is less than a preset light parameter in the single nighttime period; and
adjust a light parameter of the light source device in a nighttime period to a fourth light parameter if the total amount of light received in all the daytime periods is less than a lower threshold of the total amount of light in the daytime periods, wherein the fourth light parameter in a single nighttime period is greater than a preset light parameter in the single nighttime period.

15. The terminal according to claim 14, wherein
after determining the light parameter thresholds in the awake time period and the sleep time period, the processor is further caused to adjust a percentage of a target type of light emitted by the light source device to 0 when the current sub-period is a sleep latency, wherein the target type of light relates to the regulation of the circadian rhythm, and the sleep latency includes the first sub-period or the second sub-period comprised in the awake time period and before and adjacent to the sleep time period.

16. The terminal according to claim 15, further comprising:
a transceiver, wherein
the transceiver is configured to send a light adjustment instruction to a target terminal, and
the light adjustment instruction instructs the target terminal to adjust the light parameter of the light emitted by the light source device.

17. A computer-readable storage medium having computer readable instructions stored therein that, when executed by a processor associated with a terminal, cause the processor to provide execution comprising:
determining an awake time period and a sleep time period of a user, wherein the awake time period and the sleep time period each include at least a first sub-period and/or a second sub-period;
determining light parameter thresholds in the awake time period and the sleep time period;
obtaining a light parameter in a current time period, wherein the current time period is the awake time period or the sleep time period; and
adjusting based on the light parameter and the light parameter thresholds in the current time period, a light parameter of light emitted by a light source device, wherein
the light parameter thresholds include a lower light parameter threshold and an upper light parameter threshold, and
adjusting the light parameter of light emitted by the light source device comprises:
if a light parameter in a current sub-period is less than the lower light parameter threshold in the current sub-period, adjusting, by the terminal, the light parameter of light emitted by the light source device, in a next sub-period of the current sub-period, to a first light parameter, wherein the current sub-period includes the first sub-period or the second sub-period, and the first light parameter is greater than the light parameter in the current sub-period; and
if a light parameter in a current sub-period is greater than the upper light parameter threshold in the current sub-period, adjusting, by the terminal, the light parameter of light emitted by the light source device, in a next sub-period of the current sub-period, to a second light parameter, wherein the second light parameter is less than the light parameter in the current sub-period, wherein adjusting the light parameter of light emitted by a light source device regulates the circadian rhythm of the user; and the light source device is configured for disposal inside the terminal or configured as an independent device communicating with the terminal.

* * * * *